US007001909B2

United States Patent
Ibrahim et al.

(10) Patent No.: US 7,001,909 B2
(45) Date of Patent: *Feb. 21, 2006

(54) SUBSTITUTED HETEROCYCLIC COMPOUNDS

(75) Inventors: Prabha Ibrahim, Mountain View, CA (US); Kevin Shenk, Palo Alto, CA (US); Elfatih Elzein, Fremont, CA (US); Venkata Palle, Gurgaon (IN); Jeff Zablocki, Mountain View, CA (US); Kenneth S. Rehder, Durham, NC (US)

(73) Assignee: CV Therapeutics, Inc., Palo Alto, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 10/346,684

(22) Filed: Jan. 17, 2003

(65) Prior Publication Data

US 2003/0176447 A1    Sep. 18, 2003

Related U.S. Application Data

(63) Continuation-in-part of application No. 10/198,237, filed on Jul. 18, 2002.

(60) Provisional application No. 60/306,621, filed on Jul. 19, 2001.

(51) Int. Cl.
A61K 31/497 (2006.01)
(52) U.S. Cl. .......................... 514/254.02; 514/254.03; 514/268.4; 514/269.1; 514/270.1; 544/367; 544/368; 544/369
(58) Field of Classification Search ................ 514/338, 514/340, 342, 254.02, 254.03; 546/269.1, 546/268.4, 270.1; 544/368, 367, 369
See application file for complete search history.

(56) References Cited

U.S. PATENT DOCUMENTS

| 4,567,264 | A  | 1/1986 | Kluge et al. |
| 6,451,798 | B1 | 9/2002 | Varkhedkar et al. |
| 6,552,023 | B1 | 4/2003 | Zablocki et al. |
| 6,573,264 | B1 | 6/2003 | Zablocki et al. |

FOREIGN PATENT DOCUMENTS

WO    WO 01/62744    8/2001

OTHER PUBLICATIONS

Urbain, M. et al 'Cardiovascular potential of piperazinoisopropanoloxy derivatives of pyridoxine' CA 98:46434 (1983).*
Berthold, R. et al '(Aryloxy)hydroxypropyl heterocycles' CA 106:84635 (1987).*
Shaiee, A. et al 'Microbial synthesis of HIV protease inhibitors' CA 125:114698 (1996).*
Lloyd, R. Jr. 'Drug-directed mutagenesis/drug-driven selection for lethal mutants' CA 131:82953 (1999).*
Dressman, BA et al 'Aromatic and heterocyclic amides as HIV protease inhibitors' CA 124:317888 (1996).*
Berthold, R. et al '3-Aminopropoxyaryl derivatives' CA 105:172505 (1986).*
Fan, Y. et al 'Syntheses of 1-(2-hydroxy-3-aryloxypropyl)-4-aryolpiperazines' CA 108:5971 (1988).*
Suzuki T et al: "Structure-activity relationship of newly synthesized quinoline derivatives for reversal of multidrug resistance in cancer.", Journal of Chemistry, vol. 40, No. 13, 1997, pp. 2047-2052, XP000924067, the whole document, particularly p. 2049, table 2, compound 5.
Zacharowski K et al: "Ranolazine, a partial fatty acid oxidation inhibitor, reduces myocardial infaret size and cardiac troponin T release in the rat." . European Journal of Pharmacology, vol. 418, No. 1-2, Apr. 20, 2001, pp. 105-110, XP002215620, the whole document.
Lopaschuk G D: "Treating ischemic heart disease by pharmacologically improving cardiac energy metabolism", The American Journal of Cardiology, vol 82, No. 5A, Sep. 3, 1997, pp. 14K-17K, XP002215621, the whole document.

* cited by examiner

*Primary Examiner*—Amelia A. Owens
(74) *Attorney, Agent, or Firm*—J. Elin Hartrum

(57) ABSTRACT

Disclosed are novel heterocyclic derivatives, useful for the treatment of various disease states, in particular cardiovascular diseases such as atrial and ventricular arrhythmias, intermittent claudication, Prinzmetal's (variant) angina, stable and unstable angina, exercise induced angina, congestive heart disease, and myocardial infarction. The compounds are also useful in the treatment of diabetes, and for increasing HDL plasma levels in mammals.

35 Claims, No Drawings

SUBSTITUTED HETEROCYCLIC COMPOUNDS

FIELD OF THE INVENTION

This is a Continuation in Part of U.S. patent application Ser. No. 10/198,237, the complete disclosure of which is hereby incorporated by reference.

The present invention relates to novel heterocyclic derivatives, in particular piperazine and piperidine derivatives, and to their use in the treatment of various disease states, in particular cardiovascular diseases such as atrial and ventricular arrhythmias, intermittent claudication, Prinzmetal's (variant) angina, stable and unstable angina, exercise induced angina, congestive heart disease, ischemia, reperfusion injury, diabetes, myocardial infarction, and for increasing HDL levels in plasma while lowering LDL levels. The invention also relates to methods for their preparation, and to pharmaceutical compositions containing such compounds.

BACKGROUND

Certain classes of piperazine compounds are known to be useful for the treatment of cardiovascular diseases, including arrhythmias, angina, myocardial infarction, and related diseases such as intermittent claudication. For example, U.S Pat. No. 4,567,264 discloses a class of substituted piperazine compounds that includes a compound known as ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the above disease states.

Despite the desirable properties demonstrated by ranolazine, which is a very effective cardiac therapeutic agent, believed to function as a fatty acid oxidation inhibitor, there remains a need for compounds that have similar therapeutic properties to ranolazine, but are more potent and have a longer half-life.

SUMMARY OF THE INVENTION

It is an object of this invention to provide novel substituted piperazine and piperidine compounds with good therapeutic half-lives. Accordingly, in a first aspect, the invention relates to compounds of Formula I:

Formula I

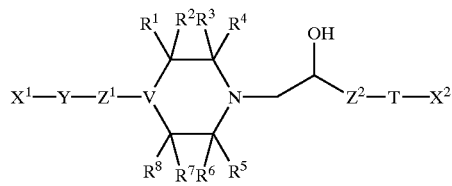

wherein:
$R^1$, $R^2$, $R^3$, $R^4$, $R^5$, $R^6$, $R^7$, and $R^8$ are hydrogen, lower alkyl, or —C(O)R; in which R is —$OR^9$ or —$NR^9R^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —$(CR^{12}R^{13})_n$—, in which n is 1, 2 or 3, and $R^{12}$ and $R^{13}$ are independently hydrogen or lower alkyl;

with the proviso that the maximum number of carbonyl groups is 2;
the maximum number of —C(O)$NR^9R^{10}$ groups is 1; and
the maximum number of bridging groups is 1;
T is oxygen, sulfur, or $NR^{11}$, in which $R^{11}$ is hydrogen or lower alkyl;
V is —N<, —CH<, or —N—CH<;
$X^1$ is hydrogen, optionally substituted lower alkyl, optionally substituted cycloalkyl, optionally substituted aryl, or optionally substituted heteroaryl;
$X^2$ is optionally substituted aryl or optionally substituted heteroaryl;
Y is optionally substituted monocyclic heteroarylenyl; and
$Z^1$ and $Z^2$ are independently optionally substituted alkylene of 1–4 carbon atoms.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that is amenable to treatment by a fatty acid oxidation inhibitor. Such diseases include, but are not limited to, protection of skeletal muscles against damage resulting from trauma, intermittent claudication, shock, and cardiovascular diseases including atrial and ventricular arrhythmias, Prinzmetal's (variant) angina, stable angina, exercise induced angina, congestive heart disease, diabetes, myocardial infarction, and for increasing HDL levels in plasma while lowering LDL levels. The compounds of Formula I can also be used to preserve donor tissue and organs used in transplants.

A fourth aspect of this invention relates to methods of preparing the compounds of Formula I.

Of the compounds of Formula I, one preferred class includes those in which V is nitrogen, particularly those compounds in which $Z^1$ and $Z^2$ are lower alkylene, more especially methylene, and T is oxygen. A preferred group within this class includes those compounds in which $R^1$, $R^2$, $R^3$, $R^4$, $R^5$, $R^6$, $R^7$ and $R^8$ are independently chosen from hydrogen and methyl, particularly where $R^1$, $R^2$, $R^3$, $R^4$, $R^5$, $R^6$, $R^7$ and $R^8$ are all hydrogen, or where $R^1$, $R^2$, $R^3$, $R^5$, $R^6$, $R^7$ and $R^8$ are all hydrogen and $R^4$ is methyl. A preferred subgroup includes those compounds in which $X^1$ is optionally substituted aryl or optionally substituted heteroaryl, more especially where $X^1$ is optionally substituted phenyl. Within this subgroup preferred is when $X^2$ is optionally substituted phenyl or optionally substituted bicyclic heteroaryl, particularly where $X^2$ is optionally substituted bicyclic heteroaryl.

More preferred within this subgroup are those compound in which Y is a diradical derived from pyrazole, 1,2-oxazole, 1,3-oxazole, 1,3-thiazole, 1,2,4-oxadiazole, or 1,3,4-oxadiazole, more especially where $X^1$ is phenyl optionally substituted by lower alkyl, lower alkoxy, halogen, or trifluoromethyl and $X^2$ is chosen from 2-methylbenzo-1,3-thiazol-5-yl, 2-cyclohexylbenzo-1,3-thiazol-5-yl, 2-phenylbenzo-1,3-thiazol-5-yl, 2-phenylbenz-1,3-oxazol-5-yl, or 2-methoxyphenyl. Most preferred are those compounds in which $X^2$ is 2-methylbenzo-1,3-thiazol-5-yl and $X^1$—Y— is 3-(4-t-butylphenyl)-1,2,4-oxadiazol-5-yl, or $X^1$—Y— is 5-(4-trifluoromethylphenyl)-1,2,4-oxadiazol-3-yl, or $X^1$—Y— is 5-(4-chlorophenyl)-1,2-oxazol-3-yl, or $X^1$—Y— is 5-(4-

(trifluoromethyl)phenyl)-isoxazol-3-yl, or $X^1$—Y— is 2-(4-(trifluoromethyl)phenyl)-oxazol-4-yl.

Preferred compounds include:

(2S)-3-[(2S)-2-methyl-4-({5-[4-chlorophenyl]isoxazol-3-yl}methyl)piperazinyl]-1-(2-methylbenzothiazol-5-yloxy)propan-2-ol;

(2S)-3-[(2S)-2-methyl-4-({5-[4-(trifluoromethyl)phenyl](1,2,4-oxadiazol-3-yl)}methyl)piperazinyl]-1-(2-methylbenzothiazol-5-yloxy)propan-2-ol;

(2S)-3-[(2S)-2-methyl-4-({5-[4-phenylphenyl](1,2,4-oxadiazol-3-yl)}methyl)piperazinyl]-1-(2-methylbenzothiazol-5-yloxy)propan-2-ol;

(2S)-3-[(2S)-2-methyl-4-({5-[2-chlorophenyl]isoxazo-3-yl}methyl)piperazinyl]-1-(2-methylbenzothiazol-5-yloxy)propan-2-ol;

(2S)-3-{(3S)-3-methyl-4-[(3-(4-methoxyphenyl)isoxazol-5-yl)methyl]piperazinyl}-1-(2-methylbenzothiazol-5-yloxy)propan-2-ol;

(2S)-3-{(3S)-3-methyl-4-[(5-(3,4-dichlorophenyl)isoxazol-3-yl)methyl]piperazinyl}-1-(2-methylbenzothiazol-5-yloxy)propan-2-ol;

(2S)-3-{(3S)-3-methyl-4-[(5-(2-chlorophenyl)isoxazol-3-yl)methyl]piperazinyl}-1-(2-methylbenzothiazol-5-yloxy)propan-2-ol;

(2S)-3-((2S)-4-{[5-(3,4-dichlorophenyl)isoxazol-3-yl]methyl}-2-methylpiperazinyl)-1-(2-methylbenzothiazol-5-yloxy)propan-2-ol;

(2S)-3-{(2S)-2-methyl-4-[(3-phenylisoxazol-5-yl)methyl]piperazinyl}-1-(2-methylbenzothiazol-5-yloxy)propan-2-ol;

(2S)-3-{(2S)-2-methyl-4-[(3-(4-methoxyphenyl)isoxazol-5-yl)methyl]piperazinyl}-1-(2-methylbenzothiazol-5-yloxy)propan-2-ol;

3-{(2S)-2-methyl-4-[(5-phenylisoxazol-3-yl)methyl]piperazinyl}(2S)-1-(2-methylbenzothiazol-5-yloxy)propan-2-ol;

(2S)-3-{(2S)-2-methyl-4-[(3-(2-thienyl)(1,2,4-oxadiazol-5-yl))methyl]piperazinyl}-1-(2-methylbenzothiazol-5-yloxy)propan-2-ol;

(2S)-3-[(2S)-2-methyl-4-({2-[4-(trifluoromethyl)phenyl](1,3-oxazol-5-yl)}methyl)piperazinyl]-1-(2-methylbenzothiazol-5-yloxy)propan-2-ol;

(2S)-3-{(3S)-3-methyl-4-[(5-(4-chlorophenyl)isoxazol-3-yl)methyl]piperazinyl}-1-(2-methylbenzothiazol-5-yloxy)propan-2-ol;

(2S)-3-((3S)-3-methyl-4-{[5-(4-trifluoromethylphenyl)isoxazol-3-yl]methyl}-piperazinyl)-1-(2-methylbenzothiazol-5-yloxy)propan-2-ol; and (2S)-3-((3S)-3-methyl-4-{[5-(4-phenylphenyl)isoxazol-3-yl]methyl}piperazinyl)-1-(2-methylbenzothiazol-5-yloxy)propan-2-ol.

Definitions and General Parameters

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamnino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1 to 6 carbon atoms.

The term "substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1–5 atoms or groups independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH($NH_2$)$CH_2$—), methylaminoethylene (—CH(NHMe)$CH_2$—), 2-carboxypropylene isomers (—$CH_2$CH($CO_2$H)$CH_2$—), ethoxyethyl (—$CH_2$$CH_2$O—$CH_2$$CH_2$—), ethylmethylaminoethyl (—$CH_2$$CH_2$N($CH_3$)$CH_2$$CH_2$—), 1-ethoxy-2-(2-ethoxyethoxy)ethane (—$CH_2$$CH_2$O—$CH_2$$CH_2$—O$CH_2$$CH_2$—O$CH_2$$CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH═$CH_2$), 1-propylene or allyl (—$CH_2$CH═$CH_2$), isopropylene (—C($CH_3$)═$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —$CH_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or, heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, and a group —Y-Z, in which Y is optionally substituted alkylene and Z is alkenyl, cycloalkenyl, or alkynyl, Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo [2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl, furyl, oxadiazolyl, oxazolyl, isoxazolyl, pyrazolyl) or multiple condensed rings (e.g., bicyclic heteroaryl groups, such as indolizinyl, benzothiazolyl, benzoxazolyl, benzothienyl, and the like). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, thiazole, isothiazole, phenazine, isoxazole, phenoxazine, phenothiazine, imidazolidine, imidazoline, and the like as well as N-alkoxy-nitrogen containing heteroaryl compounds.

The term "heteroarylene" or "heteroarylenyl" refers to a diradical of a heteroaryl group as defined above. This term is exemplified by groups such as 3,5-[1,2,4]oxadiazolenyl, 2,4-[1,3]oxazolenyl, 2,5-[1,3]oxazolenyl, 3,5-isoxazolylenyl, 3,4-pyrazolenyl, 3,5-pyrazolenyl, 2,4-thiazolenyl, and the like. For example, 3,5-[1,2,4]oxadiazolenyl in the context of a compound of Formula I is represented as:

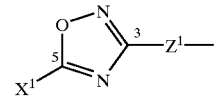

Unless otherwise constrained by the definition for the heteroaryl or heteroarylene substituent, such heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and polymorphs and prodrugs of such compounds. Additionally, the compounds of the invention may possess one or more asymmetric centers, and can be produced, as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Fatty acid oxidation inhibitors" refers to compounds that suppress ATP production from the oxidation of fatty acids and consequently stimulate ATP production from the oxidation of glucose and lactate. In the heart, most of the ATP production is acquired through the metabolism of fatty acids. The metabolism of glucose and lactate provides a lesser proportion of ATP. However, the generation of ATP from fatty acids is less efficient with respect to oxygen consumption than the generation of ATP from the oxidation of glucose and lactate. Thus, the use of fatty acid oxidation inhibitors results in more energy production per molecule of oxygen consumed, allowing the heart to be energized more efficiently. Fatty acid oxidation inhibitors are especially useful, therefore, for treating an ischemic environment in which oxygen levels are reduced.

Nomenclature

The naming and numbering of the compounds of the invention is illustrated with a representative compound of Formula I in which $R^1$, $R^2$, $R^3$, $R^4$, $R^5$, $R^6$, $R^7$, and $R^8$ are hydrogen, T is oxygen, $X^1$ is 4-t-butylphenyl, $X^2$ is 2-methylbenzothiazol-5-yl, Y is 1,2,4-oxadiazole, and $Z^1$ and $Z^2$ are methylene:

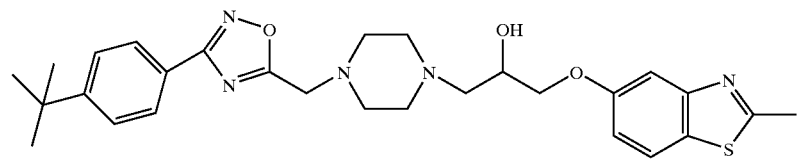

which is named:
3-[4-({3-[4-(tert-butyl)phenyl](1,2,4-oxadiazol-5-yl)}methyl)piperazinyl]-1-(2-methylbenzothiazol-5-yloxy)propan-2-ol Synthesis of the Compounds of Formula I One method of preparing the compounds of Formula I is shown in Reaction Scheme I.

REACTION SCHEME I

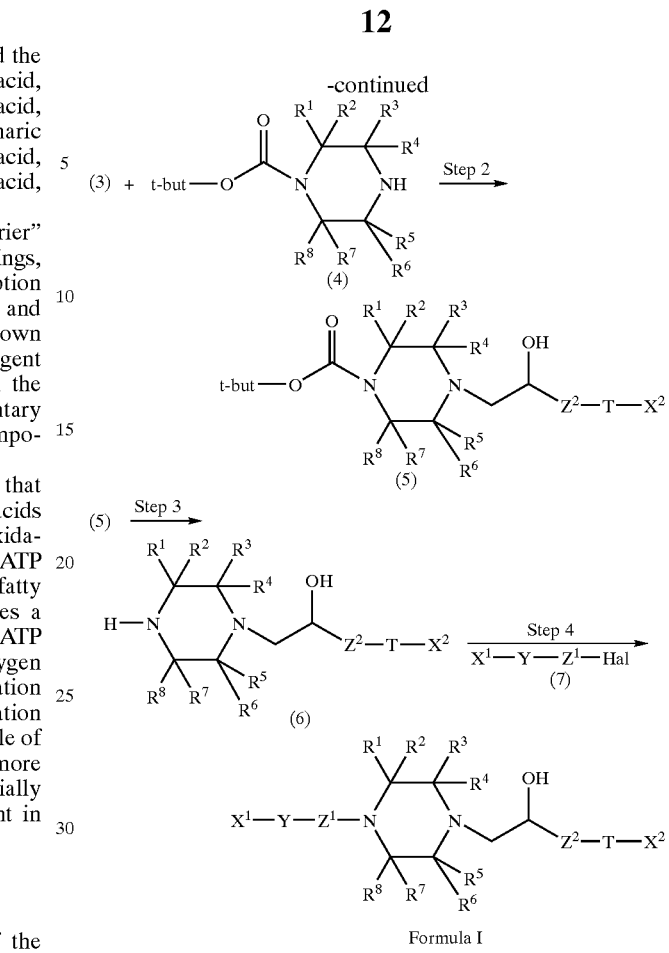

in which $R^1$, $R^2$, $R^3$, $R^4$, $R^5$, $R^6$, $R^7$, $R^8$, T, $X^1$, $X^2$, Y, $Z^1$, and $Z^2$ are as defined in the Summary of the Invention, Hal is halogen, and t-but is tertiary butyl.

Starting Materials

The compounds of formula (1), (2), and (4) are either commercially available or can be made by conventional methods well known to those of ordinary skill in the art. For example, the precursor to a compound of formula (4) where $R^1$ and $R^5$ when taken together represent a bridging methylene group, i.e.;

is commercially available [(1S,4S)-(+)-2,5-diazabicyclo[2.2.1]heptane], or can be made by a procedure disclosed in J. Org. Chem., 1990, 55, 1684–7. Similarly, the precursor to a compound of formula (4) where $R^1$ and $R^5$ when taken together represent a bridging ethylene group, and the precursor to a compound of formula (4) where $R^1$ and $R^7$ when taken together represent a bridging ethylene group, can be made by published procedures found in J. Med. Chem., 1974, 17, 481–7. The precursor to a compound of formula (4) in which $R^1$, $R^2$, $R^3$, $R^4$, $R^5$, $R^6$, and $R^7$ are hydrogen and $R^8$ is —C(O)NH$_2$ is prepared from piperazine-2-carboxamide, a commercially available compound.

Step 1—Preparation of Formula (3)

The compound of formula (3) is prepared conventionally by reaction of a compound of formula (1), for example 5-hydroxy-2-methylbenzothiazole, with an epoxide of formula (2), which may be racemic or chiral. In general, the two compounds are mixed in an inert solvent, preferably a ketone, for example acetone, and a tertiary organic base or an inorganic base, preferably potassium carbonate, at a temperature of about reflux, for about 8–48 hours, preferably overnight. When the reaction is substantially complete, the product of formula (3) is isolated by conventional means, for example by filtration, removal of the solvent under reduced pressure, followed by chromatography of the residue on silica gel. Alternatively, after filtration the product can be crystallized from the filtrate.

Step 2—Preparation of Formula (5)

The compound of formula (3) is then reacted with a protected piperazine of formula (4). In general, the two compounds are mixed in an inert solvent, preferably a halogenated solvent, for example methylene chloride, optionally in the presence of a catalyst, for example ytterbium (III) trifluoromethanesulfonate. In the presence of a catalyst the reaction is conducted at about 0–30° C., preferably at about room temperature, for about 8–48 hours, preferably overnight. In the absence of a catalyst, the mixture is refluxed for a similar period of time in ethanol in the presence of triethylamine. When the reaction is substantially complete, the product of formula (5) is isolated by conventional means, for example by removal of the solvent under reduced pressure, followed by chromatography of the residue on silica gel.

Step 3—Preparation of Formula (6)

The compound of formula (5) is then deprotected by hydrolyzing the t-butyl ester. In general, the compound of formula (5) is dissolved in a mixture of an inert solvent, preferably a halogenated solvent, for example methylene chloride, and a strong acid, for example trifluoroacetic acid. The reaction is conducted at about 0–30° C., preferably at about room temperature, for about 8–48 hours, preferably overnight. When the reaction is substantially complete, the product of formula (6) is isolated by conventional means, for example by adding a base to remove excess acid, and removal of the solvent under reduced pressure.

Step 4—Preparation of a Compound of Formula I

The compound of formula (6) is then reacted with a compound of formula (7) ($X^1$—Y-$Z^1$-Hal). Examples of such compounds are 3-(4-trifluoromethylphenyl)-5-chloromethyl-1,2,4-oxadiazole, 5-bromomethyl-4-methyl-2-phenyl-1,2,3-triazole, or 4-chloromethyl-2-(4-trifluoromethylphenyl)-1,3-thiazole, and the like. Such compounds are either commercially available, prepared by means well known in the art (see, for example, see J. Med. Chem, 1996, 39, 237–243) or prepared as shown herein. In general, the two compounds are mixed in an inert solvent, preferably a protic solvent, for example ethanol, in the presence of an inorganic or tertiary organic base, preferably triethylamine. The reaction is conducted at about 30–100° C., preferably at about reflux, for about 8–48 hours, preferably overnight. When the reaction is substantially complete, the product of Formula I is isolated by conventional means, for example by removal of the solvent under reduced pressure, followed by chromatography.

A modified procedure is preferred for preparing compounds of Formula I in which $R^8$ is lower alkyl and $R^1$–$R^7$ are hydrogen. An example where $R^8$ is methyl is shown in Reaction Scheme IA.

REACTION SCHEME IA

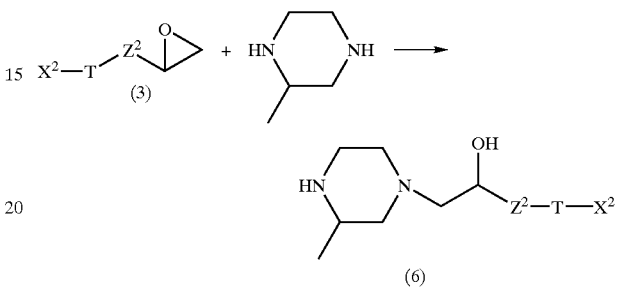

Step 1—Preparation of Formula (6)

The compound of formula (3) is reacted with 2-methylpiperazine. In general, the two compounds are mixed in a protic solvent, for example ethanol. The reaction is conducted at about 5–100° C., preferably at about 80° C., for about 1–12 hours, preferably about 5 hours. When the reaction is substantially complete, the product of formula (6) is isolated by conventional means, for example by removal of the solvent under reduced pressure, followed by chromatography of the residue on silica gel.

The compound of formula (6) is then reacted with a compound of formula (7) as described above in Reaction Scheme I, step 4, to provide a compound of Formula I in which $R^1$, $R^2$, $R^3$, $R^4$, $R^5$, $R^6$ and $R^7$ are hydrogen and $R^8$ is methyl.

A different procedure is preferred for preparing compounds of Formula I in which $R^4$ is lower alkyl and $R^1$–$R^3$ and $R^5$–$R^8$ are hydrogen. An example where $R^4$ is methyl is shown in Reaction Scheme IB.

REACTION SCHEME IB

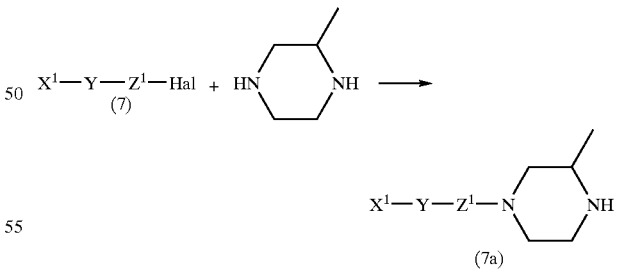

Step 1—Preparation of Formula (7a)

The compound of formula (7) is reacted with 2-methylpiperazine. In general, the two compounds are mixed in an inert solvent, preferably a protic solvent, for example ethanol, in the presence of an inorganic or tertiary organic base, preferably triethylamine. The reaction is conducted at about 30–100° C., preferably at about 80° C., for about 2–12 hours, preferably about 8 hours. When the reaction is substantially complete, the product of formula (7a) is isolated by conventional means, for example by removal of the solvent under reduced pressure, followed by chromatography.

The compound of formula (7a) is then reacted with an epoxide of formula (3) as described in Reaction Scheme I, step 2, to provide a compound of Formula I in which $R^1$, $R^2$, $R^3$, $R^5$, $R^6$, $R^7$ and $R^8$ are hydrogen and $R^4$ is methyl.

An alternative synthesis of the compounds of Formula I where Y is a 1,2,4-oxadiazole derivative is shown in Reaction Scheme II.

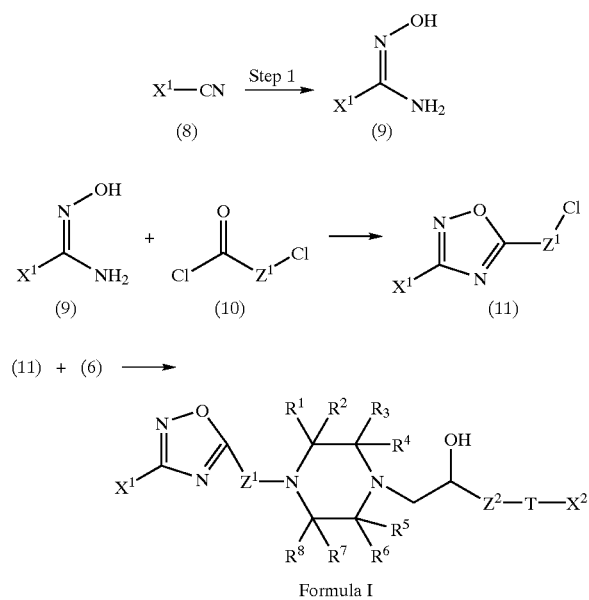

The compound of formula (9) is prepared by a known reaction, by reacting a nitrile of the formula $X^1CN$ with hydroxylamine hydrochloride in ethanol, in the presence of a tertiary base, preferably triethylamine, at about 50–100° C.

The compound of formula (9) is reacted with a chloroalkanoyl chloride of formula (10), for example chloroacetyl chloride, in an inert solvent, for example dichloromethane, at about −10 to −30° C., followed by reaction at about 85° C., to provide a compound of formula (11).

The compound of formula (11) is then reacted with a compound of formula (6) in the same manner as shown in Reaction Scheme I. Alternatively, the compound of formula (11) can be reacted with tert-butyl piperazine carboxylate, which is then deprotected by conventional means (acid conditions). The compound thus produced is then reacted with an epoxide of formula (3) as shown in Reaction Scheme I, to provide a compound of Formula I.

This provides a compound of Formula I in which a 3-substituted[1,2,4]oxadiazol-5-yl is attached to a piperazine. To prepare the corresponding 5-substituted-[1,2,4] oxadiazol-3-yl derivative, a compound of formula (9a) is reacted with an acid chloride derivative $X^1C(O)Cl$ to give a 3-chloromethyl derivative of a [1,2,4]oxadiazole of formula (11a), which is then reacted with a compound of formula (6) to give a compound of Formula I in which Y is a 5-substituted[1,2,4]oxadiazol-3-yl, as shown in Reaction Scheme III.

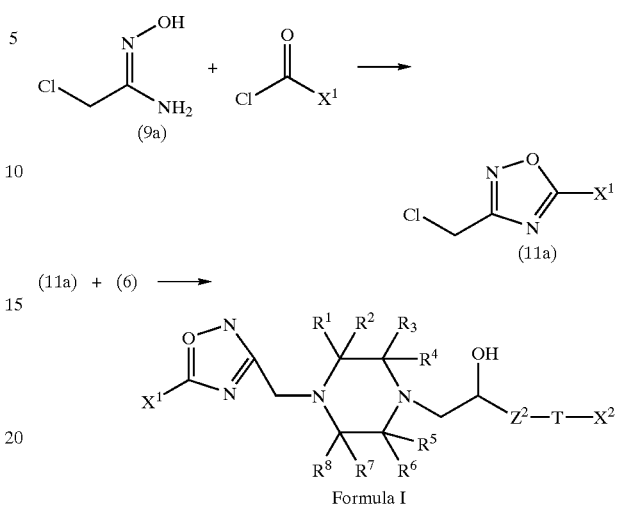

The chloromethyl compound of formula (9a) is prepared by a known reaction, by reacting chloroacetonitrile with hydroxylamine hydrochloride under aqueous conditions, in the presence of a base, preferably sodium carbonate, at about 0° C.

The 2-chloroacetoxamidoxime of formula (9a) thus formed is reacted with an acid chloride of formula $X^1C(O) Cl$ in the presence of a base, preferably a hindered tertiary base, in an inert solvent, for example toluene, at about room temperature overnight. The product is isolated, and heated at about 80–120° C. for about 2–3 days. When the reaction is substantially complete, the product of formula (11a) is isolated by conventional means.

The compound of formula (11a) is then reacted with a compound of formula (6), prepared as shown above. In general, the two compounds are mixed in an inert solvent, preferably a protic solvent, for example ethanol, in the presence of an inorganic or tertiary organic base, preferably triethylamine. The reaction is conducted at about 30–100° C., preferably at about reflux, for about 24–72 hours, preferably about 48 hours. When the reaction is substantially complete, the product of Formula I is isolated by conventional means, for example by removal of the solvent under reduced pressure, followed by chromatography.

Alternatively, the compound of formula (11a) can be reacted with tert-butyl piperazine carboxylate, which is then deprotected by conventional means (acid conditions). The compound thus produced is then reacted with an epoxide of formula (3) as shown in Reaction Scheme I, to provide a compound of Formula I.

A slightly different reaction sequence is used to prepare compounds of Formula I in which Y is an optionally substituted oxazole, as shown in Reaction Scheme IV.

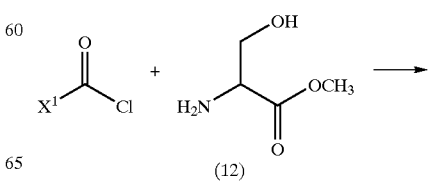

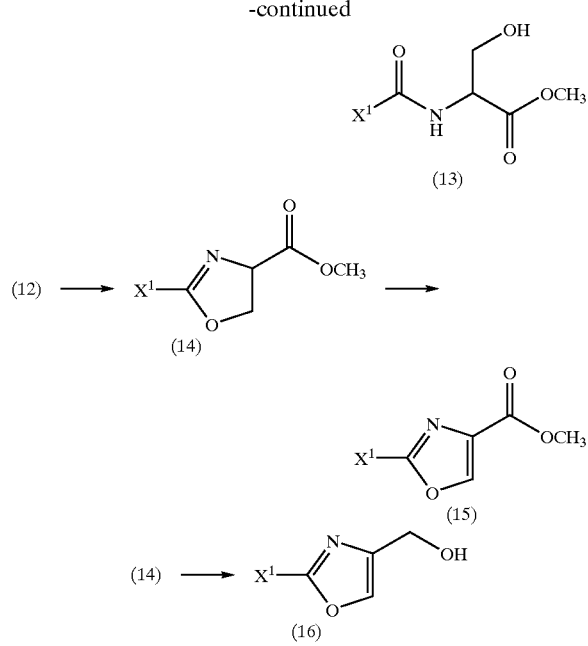

Step 1—Preparation of a Compound of Formula (13)

A compound of formula X¹C(O)Cl, is reacted with commercially available methyl 2-amino-3-hydroxypropanoate (12). In general, the two compounds are mixed in an inert solvent, for example dichloromethane, in the presence of an inorganic or tertiary organic base, preferably triethylamine. The reaction is initially conducted at about 0° C. for about 5 minutes, then at about room temperature for about 30 minutes. When the reaction is substantially complete, the product of formula (13) is isolated by conventional means, for example by removal of the solvent under reduced pressure, followed by chromatography.

Step 2—Preparation of a Compound of Formula (14)

The compound of formula (13) is then cyclized by reaction with diisopropylazodicarboxylate, or the like, in the presence of triphenylphosphine, to provide a 4-carbomethoxy-1,3-oxazoline of formula (14). The reaction is conducted in an inert solvent, for example tetrahydrofuran, at about room temperature for 1–5 days. When the reaction is substantially complete, the product of formula (14) is isolated by conventional means, for example by removal of the solvent under reduced pressure, followed by chromatography.

Step 3—Preparation of a Compound of Formula (15)

The oxazoline of formula (14) is then converted to a 4-carboxymethyl-1,3-oxazole derivative of formula (15) by reaction with 2,3-dichloro-5,6-dicyano-1,4-benzoquinone in an inert solvent, for example toluene. at about reflux for 1–2 days. When the reaction is substantially complete, the product of formula (15) is isolated by conventional means, for example by removal of the solvent under reduced pressure, followed by chromatography.

Step 4—Preparation of a Compound of Formula (16)

The carbomethoxy group of the compound of formula (15) is then reduced by conventional means to a hydroxymethyl group, to provide a compound of formula (16). For example, by reduction with lithium aluminum hydride in an ethereal solvent, for example tetrahydrofuran, at about 0° C. When the reaction is substantially complete, the product of formula (16) is isolated by conventional means, for example by quenching excess reducing agent with water, extraction with an inert solvent, for example ethyl acetate, removal of the solvent under reduced pressure, followed by chromatography.

The hydroxymethyl compound of formula (16) thus produced is reacted with a reagent capable of converting the hydroxy group to a leaving group, for example by conversion to a chloride by conventional means, or preferably by reaction with a sulfonyl chloride, for example reaction with methanesulfonyl chloride to form a mesylate. The mesylate is then reacted with a compound of formula (6) in the same manner as shown in Reaction Scheme I to provide a compound of Formula I in which Y is optionally substituted oxazole.

A different reaction sequence is used to prepare compounds of formula (7) in which Y is an optionally substituted pyrazole, as shown in Reaction Scheme V.

REACTION SCHEME V

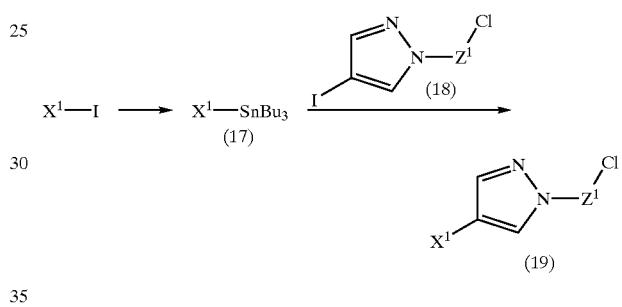

Step 1—Preparation of a Compound of Formula (17)

The commercially available iodo compound of formula X¹I is reacted with n-butyl lithium at a temperature of between about −50° C. to −80° C. in an inert solvent, for example diethyl ether, for about 1 hour. To the anion thus produced is added tri n-butylstannane, and after about 1 hour the mixture is allowed to come to room temperature. When the reaction is substantially complete, the product of formula (17) is isolated by conventional means, for example by quenching excess reducing agent with ammonium chloride/water, extraction with an inert solvent, for example ether, and removal of the solvent under reduced pressure.

Step 2—Preparation of a Compound of Formula (19)

The tin derivative of formula (17) is then mixed with an optionally substituted pyrazole derivative of formula (18). These compounds are either commercially available, or may be prepared by means well known in the art. The reaction is conducted in an inert solvent, for example acetonitrile, in the presence of triphenylarsine, copper iodide, and Pd on carbon, at a temperature of about 60–100° C., for about 1–3 days. When the reaction is substantially complete, the product of formula (19) is isolated by conventional means, for example by filtration, removal of the solvent under reduced pressure, and chromatography of the residue. The compound of formula (19) is a compound of formula (7) in which Y is 1,4-pyrazolenyl.

Compounds of formula (7) in which Y is an optionally substituted isoxazole are prepared as shown in Reaction Scheme VI.

REACTION SCHEME VI

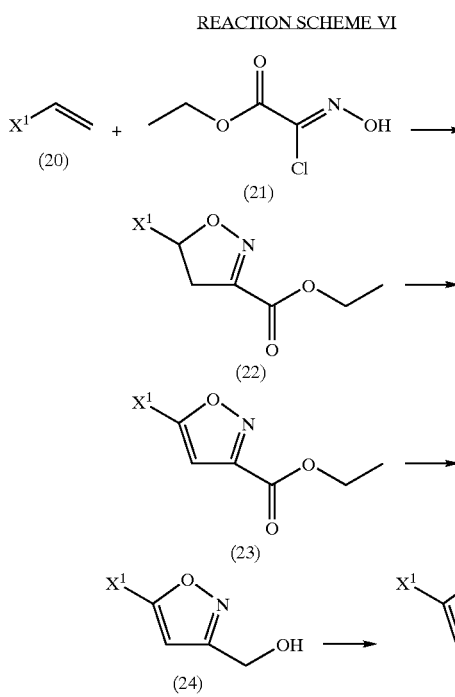

Step 1—Preparation of a Compound of Formula (22)

A vinyl derivative of formula (20) is reacted with ethyl 2-chloro-2-(hydroxyamino)acetate (21) in an inert solvent, for example tetrahydrofuran, in the presence of a tertiary base, for example triethylamine, for about 30 minutes to 4 hours. When the reaction is substantially complete, the product of formula (22) is isolated by conventional means.

Step 2—Preparation of a Compound of Formula (23)

The compound of formula (22) is then converted to a 4-carboxyethyl-1,2-oxazole derivative of formula (23) by reaction with 2,3-dichloro-5,6-dicyano-1,4-benzoquinone in an inert solvent, for example toluene. at about reflux for 1–2 days. When the reaction is substantially complete, the product of formula (23) is isolated by conventional means, for example by removal of the solvent under reduced pressure, followed by chromatography.

Step 3—Preparation of a Compound of Formula (24)

The carboxyethyl group of the compound of formula (23) is then reduced by conventional means to a hydroxymethyl group, to provide a compound of formula (24). For example, by reduction with sodium borohydride in an inert solvent, for example ethanol, at about 0° C., for about 2–8 hours. When the reaction is substantially complete, the product of formula (24) is isolated by conventional means, for example by quenching excess reducing agent with water, extraction with an inert solvent, for example ethyl acetate, removal of the solvent under reduced pressure, followed by chromatography.

Step 4—Preparation of a Compound of Formula (25)

The hydroxymethyl group of the compound of formula (24) is then converted to a chloromethyl group by conventional means, for example thionyl chloride. to provide a compound of formula (25). The reaction is carried out in an inert solvent, for example dichloromethane, at about 0° C., for about 5 minutes, followed by stirring overnight at room temperature. When the reaction is substantially complete, the product of formula (25) is isolated by conventional means, for example by removal of the solvent under reduced pressure. The compound of formula (19) is a compound of formula (7) in which Y is 5-isoxazolen-3-yl.

The compound of formula (25) is then reacted with a piperazine derivative of formula (6) in the same manner as shown in Reaction Scheme I to provide a compound of Formula I in which Y is optionally substituted 5-isoxazolen-3-yl.

An alternative method for preparing compounds of Formula I in which Y is an optionally substituted 3-isoxazolen-5-yl is shown in Reaction Scheme VII.

REACTION SCHEME VII

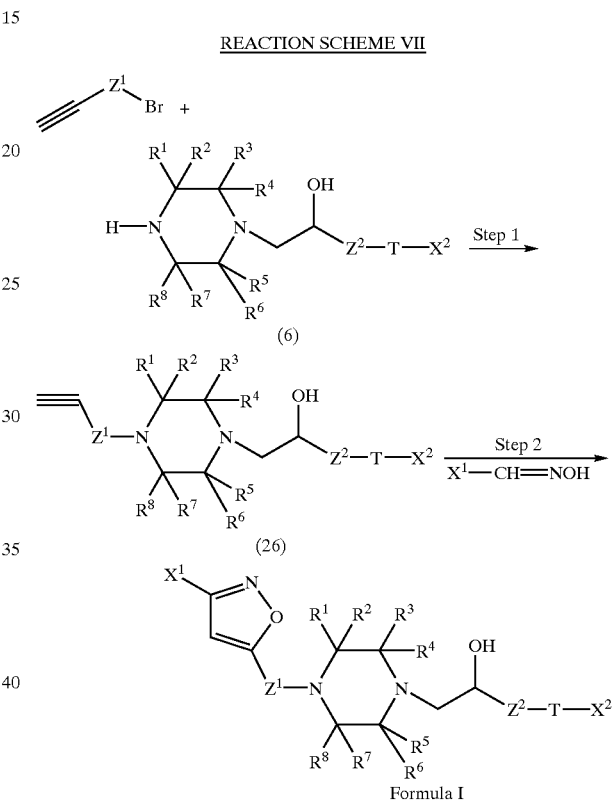

Step 1—Preparation of a Compound of Formula (26)

A compound of formula (6) is reacted with a compound of formula HC≡C-$Z^1$Br (for example, propargyl bromide). In general, the two compounds are mixed in an inert solvent, for example acetone, in the presence of an inorganic or tertiary organic base, preferably potassium carbonate. The reaction is conducted at about 30–100° C., preferably at about 40–80° C., for example reflux ion acetone, for about 1–10 hours, preferably about 5 hours. When the reaction is substantially complete, the product of formula (26) is isolated and purified by conventional means, for example by removal of the solvent under reduced pressure, followed by preparative chromatography.

Step 2—Preparation of a Compound of Formula I

The compound of formula (26) is then reacted with an nitrile oxide, prepared by oxidation of an oxime of formula $X^1$—CH=NOH. The oxidation is carried out conventionally, for example by treatment of the oxime with an oxidizing agent such as aqueous sodium hypochlorite in dichlormethane. To the nitrile oxide when formed, the compound of formula (26) is added in an inert solvent, for example dichloromethane, in the presence of an inorganic or tertiary organic base, preferably triethylamine. The reaction is carried out in a sealed vessel at an elevated temperature, preferably subjecting the sealed vessel to microwave at about 110° C. for about 4 minutes. When the reaction is substantially complete, the product of Formula I is isolated and purified by conventional means, for example by removal of the solvent under reduced pressure, followed by preparative chromatography. This provides a compound of Formula I in which Y is optionally substituted 3-isoxazolen-5-yl.

An alternative method for preparing compounds of Formula I in which Y is an optionally substituted 3-isoxazolen-5-yl is shown in Reaction Scheme VIII.

REACTION SCHEME VIII

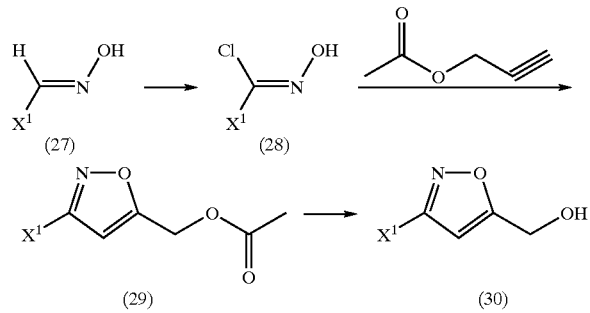

Step 1—Preparation of a Compound of Formula (28)

An oxime of formula (27), which is commercially available or prepared by means well known in the art, is reacted with a halogenating agent, for example N-chlorosuccinimide. In general, the two compounds are mixed in an inert solvent, for example dichloromethane, and reacted at about 0–30° C., preferably at about room temperature, for about 1–10 hours, preferably about 3 hours. When the reaction is substantially complete, the product of formula (28) is typically used in the next reaction with no purification.

Step 2—Preparation of a Compound of Formula (29)

The compound of formula (28) is then reacted with a propargyl ester, for example propargyl acetate. The reaction is carried out in an inert solvent, for example dichloromethane, in the presence of an inorganic or tertiary organic base, for example triethylamine. The reaction is carried out at about 0–30° C., preferably at about room temperature, for about 10–48 hours, preferably overnight. When the reaction is substantially complete, the product of formula (29) is isolated and purified by conventional means, for example by removal of the solvent under reduced pressure, followed by preparative chromatography.

Step 3—Preparation of a Compound of Formula (30)

The compound of formula (29) is then hydrolyzed to the hydroxymethyl compound of formula (30) by reaction with a strong base, for example sodium hydroxide. The reaction is carried out in a protic solvent, for example ethanol-water mixture, at a temperature of about 0–30° C., preferably at about room temperature, for about 1–6 hours, preferably for about 3 hours. When the reaction is substantially complete, the resulting solution is neutralized, and the product of formula (30) is isolated and purified by conventional means.

The hydroxy group of the compound of formula (30) is then converted to a leaving group, for example a chloro or mesyl group, by conventional means, as shown previously. The resulting halomethyl or mesylmethyl compound is then reacted with a piperazine derivative of formula (6) in the same manner as shown in Reaction Scheme I to provide a compound of Formula I in which Y is optionally substituted 3-isoxazolen-5-yl.

General Utility

The compounds of Formula I are effective in the treatment of conditions known to respond to administration of fatty acid oxidation inhibitors, including protection of skeletal muscles against damage resulting from trauma, intermittent claudication, shock, and cardiovascular diseases including atrial and ventricular arrhythmias, Prinzmetal's (variant) angina, stable angina, ischemia and reperfusion injury in cardiac, kidney, liver and the brain, exercise induced angina, congestive heart disease, and myocardial infarction. Fatty acid oxidation inhibitors have recently been shown to modify glucose levels in diabetic patients, thus providing a novel method of treating diabetes, and in particular provide an effective treatment of angina in diabetics. Fatty acid oxidation inhibitors have also been shown to raise plasma HDL levels and lower LDL levels in mammals, thus providing a method for treating coronary artery disease. The compounds of Formula I can also be used to preserve donor tissue and organs used in transplants, and may be coadministered with thrombolytics, anticoagulants, and other agents.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Compounds of Formula I may be impregnated into a stent by diffusion, for example, or coated onto the stent such as in a gel form, for example, using procedures known to one of skill in the art in light of the present disclosure. Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and are generally administered in a pharmaceutically effective amount. Preferably, for oral administration, each dosage unit contains from 1 mg to 2 g of a compound of Formula I, and for parenteral administration, preferably from 0.1 to 700 mg of a compound of Formula I. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (3)

A. Preparation of a Compound of Formula (3) in which T is Oxygen, $X^2$ is 2-Methyl-benzothiazol- 5-yl, and $Z^2$ is Methylene

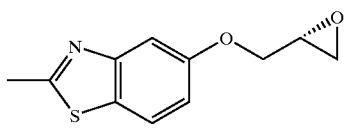

A mixture of 2-methylbenzothiazol-5-ol, a compound of formula (1) (6.0 g, 36 mmol), (S)-(+)-epichlorohydrin, a compound of formula (2) (20 ml, 182 mmol), and potassium carbonate (20 g, 144 mmol) in acetone (100 ml), was heated to reflux and allowed to stir overnight. The solution was allowed to cool and filtered through Celite 512. The filtrate was evaporated (in vacuo), to yield an oil. The oil was chromatographed on silica gel, eluting with 20% ethyl acetate/hexanes, to yield 5-[((2S)oxiran-2-yl)methoxy]-2-methylbenzothiazole as a white solid (6.2 g, 28 mmol).

B. Preparation of a Compound of Formula (3) in which T is Oxygen, $X^2$ is 2-Phenyl-benzothiazol-5-yl, and $Z^2$ is Methylene Similarly, following the procedure of 1A above, but replacing 2-methylbenzothiazol-5-ol with 2-phenylbenzoxazol-5-ol, a compound of formula (3) where $X^2$ is 2-phenylbenzoxazol-5-yl, T is oxygen, and $Z^2$ is methylene was prepared, namely 5-[((2S)oxiran-2-yl)methoxy]-2-phenyl-benzothiazole.

Similarly, the following compounds of formula (3) were prepared:
2-methoxy-1-(oxiran-2-ylmethoxy)benzene; and
2-fluoro-1-(oxiran-2-ylmethoxy)benzene.

C. Preparation of a Compound of Formula (3), varying T, $X^2$, and $Z^2$

Similarly, following the procedure of 1A above, but optionally replacing 2-methylbenzothiazol-5-ol with other compounds of formula (1), and optionally replacing (S)-(+)-epichlorohydrin with other appropriately substituted compounds of formula (2), the following compounds of formula (3) are prepared:
2-methyl-5-(R)-(oxiran-2-ylmethoxy)benzothiazole;
2-methyl-5-(RS)-(oxiran-2-ylmethoxy)benzothiazole
2-methoxy-1-(oxiran-2-ylethoxy)benzene;
2-chloro-1-(oxiran-2-ylethoxy)benzene;
2-methyl-5-(oxiran-2-ylethoxy)benzothiazole;
2-fluoro-1-(oxiran-2-ylmethoxy)benzene;
4-methoxy-1-(oxiran-2-ylmethoxy)benzene;
8-fluoro-1-(oxiran-2-ylmethoxy)naphthalene;
1-fluoro-2-(oxiran-2-ylmethoxy)naphthalene;
2-ethyl-4-(oxiran-2-yl methoxy)thiazole;
4-methyl-2-(oxiran-2-yl methoxy)imidazole;
2-methyl-5-(oxiran-2-yl methoxy)benzimidazole; and
2-phenyl-5-(oxiran-2-yl methoxy)benzimidazole.

D. Preparation of a Compound of Formula (3), varying T, $X^2$, and $Z^2$

Similarly, following the procedure of 1A above, but optionally replacing 2-methylbenzothiazol-5-ol with other compounds of formula (1), and optionally replacing (S)-(+)-epichlorohydrin with other appropriately substituted compounds of formula (2), other compounds of formula (3) are prepared.

EXAMPLE 2

Preparation of a Compound of Formula (5)

A. Preparation of a Compound of Formula (5) in which $R^1$, $R^2$, $R^3$, $R^4$, $R^5$, $R^6$, $R^7$, and $R^8$ are Hydrogen, T is Oxygen, $X^2$ is 2-Methylbenzothiazol-5-yl, and $Z^2$ is Methylene

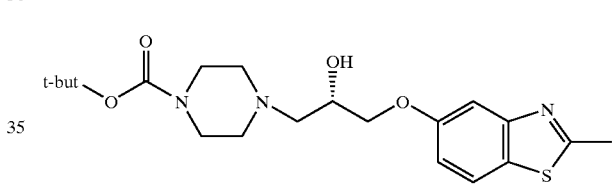

To a solution of 5-[((2S)oxiran-2-yl)methoxy]-2-methyl-benzothiazole, a compound of formula (3) (6.2 g, 28 mmol), and tert-butyl 1-piperazinecarboxylate, a compound of formula (4) (5.7 g, 31 mmol), in methylene chloride (200 ml), was added ytterbium (111) trifluoromethanesulfonate (1.73 g, 28 mmol). The resulting solution was allowed to stir at room temperature overnight. The solvent was evaporated (in vacuo), to yield a semi-solid, which was chromatographed on silica gel, eluting with 5% methanol/methylene chloride, to yield (2S)-1-(2-methylbenzothiazol-5-yloxy)butan-2-ol, tert butyl piperazinecarboxylate as a clear oil (9.5 g, 23 mmol).

B. Preparation of a Compound of Formula (5) in which $R^1$, $R^2$, $R^3$, $R^4$, $R^5$, $R^6$, $R^7$, and $R^8$ are Hydrogen, T is Oxygen, $X^2$ is 2-Phenylbenzoxazol-5-yl, and $Z^2$ is Methylene Similarly, following the procedure of 2A above, but replacing 2-methylbenzothiazol-5-ol with 2-phenylbenzoxazol-5-ol, the compound of formula (3) where $X^2$ is 2-phenylbenzoxazol-5-yl, T is oxygen, and $Z^2$ is methylene was prepared, namely 4-[2-hydroxy-3-(2-phenylbenzoxazol-5-yloxy)propyl]-piperazine-1-carboxylic acid tert-butyl ester.

Similarly, the following compounds of formula (3) were prepared:
4-[2-hydroxy-3-(2-methoxyphenoxy)propyl]-piperazine-1-carboxylic acid tert-butyl ester; and
4-[2-hydroxy-3-(2-fluorophenoxy)propyl]-piperazine-1-carboxylic acid tert-butyl ester.

C. Preparation of a Compound of Formula (5), varying $R^1$, $R^2$, $R^3$, $R^4$, $R^5$, $R^6$, $R^7$ $R^8$, T, $X^2$, and $Z^2$ Similarly, following the procedure of 2A above, but optionally replacing 2-methyl-5-(oxiran-2-ylmethoxy)benzothiazole with other compounds of formula (3), and optionally replacing tert-butyl 1-piperazinecarboxylate with other compounds of formula (4), the following compounds of formula (5) are prepared:
4-[2-hydroxy-4-(2-methoxyphenoxy)butyl]-piperazine-1-carboxylic acid tert-butyl ester;
4-[2-hydroxy-4-(2-fluorophenoxy)butyl]-piperazine-1-carboxylic acid tert-butyl ester;
4-[2-hydroxy-4-(2-methylbenzothiazol-5-yloxy)butyl]-piperazine-1-carboxylic acid tert-butyl ester.
4-[2-hydroxy-3-(2-fluorophenoxy)propyl]-piperazine-1-carboxylic acid tert-butyl ester;
4-[2-hydroxy-3-(4-methoxyphenoxy)propyl]-piperazine-1-carboxylic acid tert-butyl ester;
4-[2-hydroxy-3-(8-fluoronaphth-1-yloxy)propyl]-piperazine-1-carboxylic acid tert-butyl ester;
4-[2-hydroxy-3-(1-fluoronaphth-2-yloxy)propyl]-piperazine-1-carboxylic acid tert-butyl ester;
4-[2-hydroxy-3-(2-ethylthiazol-4-yloxy)propyl]-piperazine-1-carboxylic acid tert-butyl ester;
4-[2-hydroxy-3-(4-methylimidazol-4-yloxy)propyl]-piperazine-1-carboxylic acid tert-butyl ester;
4-[2-hydroxy-3-(2-methylbenzmiidazol-5-yloxy)propyl]-piperazine-1-carboxylic acid tert-butyl ester; and
4-[2-hydroxy-3-(2-phenylbenzimidazo-5-yloxy)propyl]-piperazine-1-carboxylic acid tert-butyl ester.

D. Preparation of a Compound of Formula (5), varying $R^1$, $R^2$, $R^3$, $R^4$, $R^5$, $R^6$, $R^7$ $R^8$, T, $X^2$, and $Z^2$ Similarly, following the procedure of 2A above, but optionally replacing 2-methyl-5-(oxiran-2-ylmethoxy)benzothiazole with other compounds of formula (3), and optionally replacing tert-butyl 1-piperazinecarboxyl ate with other compounds of formula (4), other compounds of formula (5) are prepared.

EXAMPLE 3

Preparation of a Compound of Formula (6)

A. Preparation of a Compound of Formula (6) in which $R^1$, $R^2$, $R^3$, $R^4$, $R^5$, $R^6$, $R^7$, and $R^8$ are Hydrogen, T is Oxygen, $X^2$ is 2-Methylbenzothiazol-5-yl, and $Z^2$ is Methylene

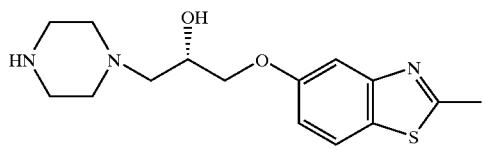

A solution of (2S)-1-(2-methylbenzothiazol-5-yloxy)butan-2-ol, tert butyl piperazinecarboxylate, a compound of formula (5) (2.0 g, 4.9 mmol), and 25% trifluoroacetic acid/methylene chloride (20 ml) was allowed- to stir at room temperature overnight. The solvent was evaporated (in vacuo) to yield an oil. The oil was diluted with acetone (20 ml) and solid potassium carbonate was added until the foaming stopped. The resulting mixture was allowed to stir overnight. The solution was filtered through Celite 512, and the filtrate was evaporated (in vacuo), to yield an oil. The oil was placed under high vacuum overnight, to yield (2S)-1-(2-methylbenzothiazol-5-yloxy)-3-piperazinylpropan-2-ol, as a clear viscous oil (3.4 g. 6.3 mmol).

B. Preparation of a Compound of Formula (6) in which $R^1$, $R^2$, $R^3$, $R^4$, $R^5$, $R^6$, $R^7$, and $R^8$ are Hydrogen, T is Oxygen, $X^2$ is 2-Phenylbenzoxazol-5-yl, and $Z^2$ is Methylene Similarly, following the procedure of 3A above, but replacing (2S)-1-(2-methylbenzothiazol-5-yloxy)butan-2-ol, tert butyl piperazinecarboxylate with 4-[2-hydroxy-3-(2-phenylbenzoxazol-5-yloxy)propyl]-piperazine-1-carboxylic acid tert-butyl ester, the compound of formula (6) where $R^1$, $R^2$, $R^3$, $R^4$, $R^5$, $R^6$, $R^7$, and $R^8$ are hydrogen, $X^2$ is 2-phenylbenzoxazol-5-yl, T is oxygen, and $Z^2$ is methylene was prepared, namely 1-(2-phenylbenzothiazol-5-yloxy)-3-piperazin-1-yl-propan-2-ol.

Similarly, the following compounds of formula (6) were prepared:
1-(2-methoxyphenoxy)-3-piperazin-1-yl-propan-2-ol; and
1-(2-fluorophenoxy)-3-piperazin-1-yl-propan-2-ol.

C. Preparation of a Compound of Formula (6), varying $R^1$, $R^2$, $R^3$, $R^4$, $R^5$, $R^6$, $R^7$ $R^8$, T, $X^2$, and $Z^2$ Similarly, following the procedure of 3A above, but replacing (2S)-1-(2-methylbenzothiazol-5-yloxy)butan-2-ol, tert butyl piperazinecarboxylate with other compounds of formula (5), the following compounds of formula (6) are prepared:
1-(2-methoxyphenoxy)-4-piperazin-1-yl-butan-3-ol;
1-(2-chlorophenoxy)-4-piperazin-1-yl-butan-3-ol;
1-(2-methylbenzothiazol-5-yloxy)-4-piperazin-1-yl-butan-3-ol;
1-(2-fluorophenoxy)-3-piperazin-1-yl-propan-2-ol;
1-(4-methoxyphenoxy)-3-piperazin-1-yl-propan-2-ol;
1-(8-fluoronaphth-1-yloxy)-3-piperazin-1-yl-propan-2-ol;
1-(1-fluoronaphth-2-yloxy)-3-piperazin-1-yl-propan-2-ol;
1-(2-ethylthiazol-4-yloxy)-3-piperazin-1-yl-propan-2-ol;
1-(4-methylimidazol-4-yloxy)-3-piperazin-1-yl-propan-2-ol;
1-(2-methylbenzimidazol-5-yloxy)-3-piperazin-1-yl-propan-2-ol; and
1-(2-phenylbenzimidazol-5-yloxy)-3-piperazin-1-yl-propan-2-ol.

D. Preparation of a Compound of Formula (6), varying $R^1$, $R^2$, $R^3$, $R^4$, $R^5$, $R^6$, $R^7$ $R^8$, T, $X^2$, and $Z^2$ Similarly, following the procedure of 3A above, but replacing 4-[2-hydroxy-3-(2-methylbenzothiazol-5-yloxy)propyl]piperazine-1-carboxylic acid tert-butyl ester with other compounds of formula (5), other compounds of formula (6) are prepared.

EXAMPLE 4

Preparation of a Compound of Formula I

A. Preparation of a Compound of Formula I in which $R^1$, $R^2$, $R^3$, $R^4$, $R^5$, $R^6$, $R^7$, and $R^8$ are Hydrogen, T is Oxygen, $X^1$ is 4-t-Butylphenyl, $X^2$ is 2-Methylbenzothiazol-5-yl, Y is 1,2,4-Oxadiazole, and $Z^1$ and $Z^2$ are Methylene

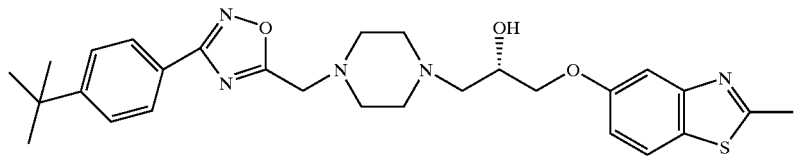

A solution of (2S)-1-(2-methylbenzothiazol-5-yloxy)-3-piperazinylpropan-2-ol, a compound of formula (6) (75 mg, 0.14 mmol), and 3-(4-tert-butylphenyl)-5-chloromethyl-1,2,4-oxadiazole (40 mg, 0.16 mmol) in 10% trimethylamine/ethanol, was heated to 73° C. and allowed to stir overnight. The solvent was evaporated under reduced pressure, and the resulting residue chromatographed by PTLC (3% methanol/methylene chloride). The resulting oil was diluted with methylene chloride and placed on the high Vac. overnight, to yield (2S)-3-[4-({3-[4-(tert-butyl)phenyl](1,2,4-oxadiazol-5-yl)}methyl)piperazinyl]-1-(2-methylbenzothiazol-5-yloxy)propan-2-ol as a white solid (52 mg, 0.09 mmol).

B. Preparation of a Compound of Formula I in which $R^1$, $R^2$, $R^3$, $R^4$, $R^5$, $R^6$, $R^7$, and $R^8$ are Hydrogen, T is Oxygen, $X^1$ is 4-t-Butylphenyl, $X^2$ is 2-Phenylbenzoxazol-5-yl, Y is 1,2,4-Oxadiazole, and $Z^1$ and $Z^2$ are Methylene Similarly, following the procedure of 4A above, but replacing (2S)-1-(2-methylbenzothiazol-5-yloxy)-3-piperazinylpropan-2-ol with (2S)-1-(2-phenylbenzoxazol-5-yloxy)-3-piperazine-1-yl-propan-2-ol, the compound of Formula I where $R^1$, $R^2$, $R^3$, $R^4$, $R^5$, $R^6$, $R^7$, and $R^8$ are hydrogen, $X^1$ is 4-t-butylphenyl, $X^2$ is 2-phenylbenzoxazol-5-yl, Y is 1,2,4-oxadiazole, T is oxygen, and $Z^1$ and $Z^2$ are both methylene, was prepared, namely 3-{4-[3-(4-t-butylphenyl)-[1,2,4]-oxadiazol-5-ylmethyl]-piperazin-1-yl}-1-(2-phenylbenzoxazol-5-yloxy)-propan-2-ol.

Similarly, the following compounds of Formula I were prepared:

(2S)-3-{4-[3-(3,5-dimethyl-isoxazol-4-yl)-[1,2,4]-oxadiazol-5-ylmethyl]-piperazin-1-yl}-1-(2-methylbenzothiazol-5-yloxy)-propan-2-ol;

(2S)-3-{4-[5-(2-methoxyphenyl))-[1,2,4]-oxadiazol-3-ylmethyl]-piperazin-1-yl}-1-(2-methylbenzothiazol-5-yloxy)-propan-2-ol;

(2S)-3-{4-[5-(4-methoxyphenyl))-[1,2,4]-oxadiazol-3-ylmethyl]-piperazin-1-yl}-1-(2-methylbenzothiazol-5-yloxy)-propan-2-ol;

(2S)-3-{4-[5-(3-trifluoromethylphenyl))-[1,2,4]-oxadiazol-3-ylmethyl]-piperazin-1-yl}-1-(2-methylbenzothiazol-5-yloxy)-propan-2-ol;

(2S)-3-{4-[5-(4-trifluoromethylphenyl))-[1,2,4]-oxadiazol-3-ylmethyl]-piperazin-1-yl}-1-(2-methylbenzothiazol-5-yloxy)-propan-2-ol;

3-[4-(2-methyl-1,3-thiazol-4-ylmethyl)-piperazin-1-yl]-1-(2-methylbenzothiazol-5-yloxy)-propan-2-ol;

3-[4-(5-methylisoxazol-3-ylmethyl)-piperazin-1-yl]-1-(2-methylbenzothiazol-5-yloxy)-propan-2-ol;

(2S)-3-{4-[2-(4-trifluoromethylphenyl)-1,3-thiazol-4-ylmethyl)-piperazin-1-yl]-1-(2-methylbenzothiazol-5-yloxy)-propan-2-ol;

(2S)-3-{4-[3-(4-chlorophenyl))-[1,2,4]-oxadiazol-5-ylmethyl]-piperazin-1-yl}-1-(2-methylbenzothiazol-5-yloxy)-propan-2-ol;

(2S)-3-{4-[2-(3,5-dimethyl-1,2-oxazol-4-yl)-[1,2,4]-oxadiazol-3-ylmethyl]-piperazin-1-yl}-1-(2-phenylbenzoxazol-5-yloxy)-propan-2-ol;

(2S)-3-{4-[5-(2-methoxyphenyl))-[1,2,4]-oxadiazol-3-ylmethyl]-piperazin-1-yl}-1-(2-phenylbenzoxazol-5-yloxy)-propan-2-ol;

(2S)-3-{4-[5-(4-methoxyphenyl))-[1,2,4]-oxadiazol-3-ylmethyl]-piperazin-1-yl}-1-(2-phenylbenzoxazol-5-yloxy)-propan-2-ol;

(2S)-3-{4-[5-(3-trifluoromethylphenyl))-[1,2,4]-oxadiazol-3-ylmethyl]-piperazin-1-yl}-1-(2-phenylbenzoxazol-5-yloxy)-propan-2-ol;

(2S)-3-{4-[5-(4-trifluoromethylphenyl))-[1,2,4]-oxadiazol-3-ylmethyl]-piperazin-1-yl}-1-(2-phenylbenzoxazol-5-yloxy)-propan-2-ol;

3-[4-(2-methyl-1,3-thiazol-4-ylmethyl)-piperazin-1-yl]-1-(2-phenylbenzoxazol-5-yloxy)-propan-2-ol;

3-[4-(5-methylisoxazol-3-ylmethyl)-piperazin-1-yl]-1-(2-phenylbenzoxazol-5-yloxy)-propan-2-ol;

(2S)-3-{4-[2-(4-trifluoromethylphenyl)-1,3-thiazol-4-ylmethyl)-piperazin-1-yl]-1-(2-phenylbenzoxazol-5-yloxy)-propan-2-ol;

(2S)-3-{4-[5-(4-chlorophenyl))-[1,2,4]-oxadiazol-3-ylmethyl]-piperazin-1-yl}-1-(2-phenylbenzoxazol-5-yloxy)-propan-2-ol;

(2S)-3-{4-[3-(3,5-dimethyl-isoxazol-4-yl)-[1,2,4]-oxadiazol-5-ylmethyl]-piperazin-1-yl}-1-(2-methoxyphenoxy)-propan-2-ol;

(2S)-3-{4-[5-(2-methoxyphenyl))-[1,2,4]-oxadiazol-3-ylmethyl]-piperazin-1-yl}-1-(2-methoxyphenoxy)-propan-2ol;

(2S)-1-{4-[5-(5-methoxyphenyl))-[1,2,4]-oxadiazol-3-ylmethyl]-piperazin-1-yl}-3-(2-methoxyphenoxy)-propan-2-ol;

(2S)-3-{4-[5-(3-trifluoromethylphenyl))-[1,2,4]-oxadiazol-3-ylmethyl]-piperazin-1-yl}-1-(2-methoxyphenoxy)-propan-2-ol;

(2S)-3-{4-[3-(3,5-dimethyl-isoxazol-4-yl)-[1,2,4]-oxadiazol-5-ylmethyl]-piperazin-1-yl}-1-(2-fluorophenoxy)-propan-2-ol;

(2S)-3-{4-[5-(2-methoxyphenyl))-[1,2,4]-oxadiazol-3-ylmethyl]-piperazin-1-yl}-1-(2-fluorophenoxy)-propan-2-ol;

(2S)-3-{4-[5-(5-methoxyphenyl))-[1,2,4]-oxadiazol-3-ylmethyl]-piperazin-1-yl}-1-(2-fluorophenoxy)-propan-2-ol;

(2S)-3-{4-[5-(3-trifluoromethylphenyl))-[1,2,4]-oxadiazol-3-ylmethyl]-piperazin-1-yl}-1-(2-fluorophenoxy)-propan-2-ol;

(2S)-1-(2-fluorophenoxy)-3-(4-{[5-(4-methoxyphenyl)(1,2,4-oxadiazol-3-yl)]methyl}piperazinyl)propan-2-ol;

(2S)-3-(4-{[5-(3,5-dimethylisoxazol-4-yl)(1,2,4-oxadiazol-3-yl)]methyl}piperazinyl)-1-(2-fluorophenoxy)propan-2-ol;

(2S)-1-(2-fluorophenoxy)-3-(4-{[5-(2-trifluoromethylphenyl)(1,2,4-oxadiazol-3-yl)]methyl}piperazinyl)propan-2-ol;

(2S)-3-(4-{[3-(4-chlorophenyl)(1,2,4-oxadiazol-5-yl)]methyl}piperazinyl)-1-(2-phenylbenzoxazol-5-yloxy)propan-2-ol;

(2S)-3-(4-{[5-(3,5-dimethylisoxazol-4-yl)(1,2,4-oxadiazol-3-yl)]methyl}-piperazinyl)-1-(2-phenylbenzoxazol-5-yloxy)propan-2-ol;

(2S)-3-(4-{[3-(2-ethylphenyl)(1,2,4-oxadiazol-5-yl)]methyl}piperazinyl)-1-(2-phenylbenzoxazol-5-yloxy)propan-2-ol;
(2S)-3-(4-{[3-(4-t-butylphenyl)(1,2,4-oxadiazol-5-yl)]methyl}piperazinyl)-1-(2-methylbenzothiazol-5-yloxy)propan-2-ol;
(2S)-3-{4-[(5-cyclohexyl(1,2,4-oxadiazol-3-yl))methyl]piperazinyl}-1-(2-methylbenzothiazol-5-yloxy)propan-2-ol;
ethyl 3-{4-[5-({4-[(2S)-2-hydroxy-3-(2-methylbenzothiazol-5-yloxy)propyl]piperazinyl}methyl)(1,2,4-oxadiazol-3-yl)]phenoxy}-3-methylbutanoate;
(2S)-2-{4-[5-({4-[(2S)-2-hydroxy-3-(2-methylbenzothiazol-5-yloxy)propyl]piperazinyl}-methyl)(1,2,4-oxadiazol-3-yl)]phenoxy}-2-methylpropanoic acid;
(2S)-2-{4-[5-({4-[(2S)-2-hydroxy-3-(2-methylbenzothiazol-5-yloxy)propyl]piperazinyl}-methyl)(1,2,4-oxadiazol-3-yl)]phenyl}-2-methylpropanoic acid;
(2S)-3-{(2S)-2-methyl-4-[(3-(2-thienyl)(1,2,4-oxadiazol-5-yl))methyl]piperazinyl}-1-(2-methylbenzothiazol-5-yloxy)propan-2-ol;
(2S)-3-[2,2-dimethyl-4-({5-[4-(trifluoromethyl)phenyl](1,2,4-oxadiazol-3-yl)}methyl)piperazinyl]-1-(2-methylbenzothiazol-5-yloxy)propan-2-ol;
3-((3R)-4-{[5-(tert-butyl)(1,2,4-oxadiazol-3-yl)]methyl}-3-methylpiperazinyl)-(2S)-1-(2-methylbenzothiazol-5-yloxy)propan-2-ol;
(2S)-3-(4-{[5-(tert-butyl)(1,2,4-oxadiazol-3-yl)]methyl}piperazinyl)-1-(2-methylbenzothiazol-5-yloxy)propan-2-ol;
(2S)-3-{4-[(2-methyl(1,3-thiazol-4-yl))methyl]piperazinyl}-1-(2-methylbenzothiazol-5-yloxy)propan-2-ol;
(2S)-3-{4-[(2-trifluoromethyl(1,3-thiazol-5-yl))methyl]piperazinyl}-1-(2-methylbenzothiazol-5-yloxy)propan-2-ol;
(2S)-1-(2-methylbenzothiazol-5-yloxy)-3-{4-[(2-phenyl(1,2,3-triazol-4-yl))methyl]piperazinyl}propan-2-ol; (6514)
(2S)-3-[(2S)-2-methyl-4-({2-[4-(trifluoromethyl)phenyl](1,3-oxazol-5-yl)}methyl)piperazinyl]-1-(2-methylbenzothiazol-5-yloxy)propan-2-ol;
(2S)-3-{(3S)-3-methyl-4-[(3-methyl-5-phenylisoxazol-4-yl)methyl]piperazinyl}-1-(2-methylbenzothiazol-5-yloxy)propan-2-ol;
(2S)-3-{(2R)-2-methyl-4-[(3-methyl-5-phenylisoxazol-4-yl)methyl]piperazinyl}-1-(2-methylbenzothiazol-5-yloxy)propan-2-ol;
(2S)-1-(2-methylbenzothiazol-5-yloxy)-3-[4-({5-methyl-2-[4-methyl-2-(trifluoromethyl)phenyl](1,3-thiazol-5-yl)}methyl)piperazinyl]propan-2-ol;
(2S)-3-[(3S)-3-methyl-4-({5-methyl-2-[4-methyl-2-(4-trifluoromethyl)phenyl](1,3-thiazol-5-yl)}methyl)piperazinyl]-1-(2-methylbenzothiazol-5-yloxy)propan-2-ol; (4) and
(2S)-3-((2S)-2-methyl-4-{[4-methyl-2-(4-trifluoromethylphenyl)(1,3-thiazol-5-yl)]methyl}piperazinyl)-1-(2-methylbenzothiazol-5-yloxy)propan-2-ol;

C. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of 4A above, but optionally replacing (2S)-1-(2-methylbenzothiazol-5-yloxy)-3-piperazinylpropan-2-ol with other compounds of formula (6), and optionally replacing 3-(4-tert-butylphenyl)-5-chloromethyl-1,2,4-oxadiazole with other compounds of formula (7), the following compounds of Formula I are prepared:
(2S)-3-{4-[5-(4-t-butylphenyl)-[1,2,4]oxadiazol-3-ylmethyl]-piperazin-1-yl}-1-(2-methyl-benzothiazo-5-yloxy)-propan-2-ol;
(2S)-3-{4-[5-(4-t-butylphenyl)-[1,2,4]oxadiazol-3-ylmethyl]-piperazin-1-yl}-1-(2-methoxyphenoxy)-butan-3-ol;
(2S)-3-{4-[5-(4-t-butylphenyl)-[1,2,4]oxadiazol-3-ylmethyl]-piperazin-1-yl }-1-(2-chlorophenoxy)-butan-3-ol;
(2S)-3-{4-[5-(4-t-butylphenyl)-[1,2,4]oxadiazol-3-ylmethyl]-piperazin-1-yl}-1-(2-methylbenzothiazol-5-yloxy)-4-piperazin-1-yl-butan-3-ol;
(2S)-3-{4-[5-(4-t-butylphenyl)-[1,2,4]oxadiazol-3-ylmethyl]-piperazin-1-yl}-1-(2-fluorophenoxy)-3-piperazin-1-yl-propan-2-ol;
(2S)-3-{4-[5-(4-t-butylphenyl)-[1,2,4]oxadiazol-3-ylmethyl]-piperazin-1-yl}-1-(2-fluorophenoxy)-propan-2-ol;
(2S)-3-{4-[5-(3-trifluoromethylphenyl)-[1,2,4]oxadiazol-3-ylmethyl]-piperazin-1-yl}-1-(4-methoxyphenoxy)-propan-2-ol;
(2S)-3-{4-[5-(4-t-butylphenyl)-[1,2,4]oxadiazol-3-ylmethyl]-piperazin-1-yl}-1-(8-fluoronaphth-1-yloxy)-propan-2-ol;
(2S)-3-{4-[5-(4-chlorophenyl)-[1,2,4]oxadiazol-3-ylmethyl]-piperazin-1-yl}-1-(1-fluoronaphth-2-yloxy)-propan-2-ol;
(2S)-3-{4-[5-(2-methoxyphenyl)-[1,2,4]oxadiazol-3-ylmethyl]-piperazin-1yl}-1-(2-ethylthiazol-4-yloxy)-propan-2-ol-;
(2S)-3-{4-[5-(4-methylimidazol-2-yl)-[1,2,4]oxadiazol-3-ylmethyl]-piperazin-1-yl}-1-(2-methylbenzothiazo-5-yloxy)-propan-2-ol;
(2S)-3-{4-[5-(2-methylbenzimidazol-5-yl)-[1,2,4]oxadiazol-3-ylmethyl]-piperazin-1-yl}-1-(2-methylbenzothiazo-5-yloxy)-propan-2-ol; and
(2S)-3-{4-[3-(2-phenylbenzimidazol-2-yl)-[1,2,4]oxadiazol-5-ylmethyl]-piperazin-1-yl}-1-(2-methylbenzothiazo-5-yloxy)-propan-2-ol.

D. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of 4A above, but optionally replacing (2S)-1-(2-methylbenzothiazol-5-yloxy)-3-piperazinylpropan-2-ol with other compounds of formula (6), and optionally replacing 3-(4-tert-butylphenyl)-5-chloromethyl-1,2,4-oxadiazole with other compounds of formula (7), other compounds of Formula I are prepared.

E. Preparation of a Compound of Formula (6) in which $R^1$, $R^2$, $R^3$, $R^4$, $R^5$ $R^6$ and $R^7$ are Hydrogen, $R^8$ is (S)-Methyl, T is Oxygen, $X^2$ is 2-Methylbenzothiazol-5-yl, and $Z^2$ is Methylene

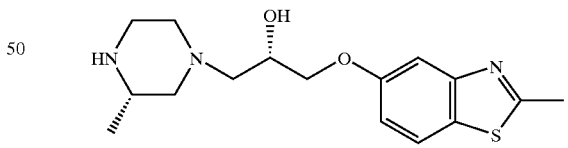

To a stirred solution of (2S)-methylpiperazine (1.0 g, 10.0 mmol) in ethanol (10 mL) was added slowly a solution of 5-[((2S)oxiran-2-yl)methoxy]-2-methylbenzothiazole (2.20 g, 10.0 mmol) in ethanol (10 mL). The resulting mixture was stirred at 80° C. under an atmosphere of nitrogen for 5 hours. It was then cooled, concentrated, and purified by chromatography (1:9 MeOH:CH$_2$Cl$_2$) to yield (2S)-3-((3S)-3-methylpiperazinyl)-1-(2-methylbenzothiazol-5-yloxy)propan-2-ol (2.28 g, M+1=322.25), which was then treated with 4N HCl in 1,4-dioxane (4 mL, 8.0 mmol) followed by evaporation in vacuum to afford the hydrochloride salt as a pale yellow solid (2.80 g, 7.6 mmol).

EXAMPLE 4A

Alternative Preparation of a Compound of Formula I

Preparation of a Compound of Formula I in which $R^1$, $R^2$, $R^3$, $R^4$, $R^5$ $R^6$ and $R^7$ are Hydrogen, $R^8$ is (S)-Methyl. T is Oxygen. $X^1$—Y— is 5-(2-Fluorophenyl)isoxazol-3-yl, $X^2$ is 2-Methylbenzothiazol-5-yl, and $Z^1$ and $Z^2$ are Methylene

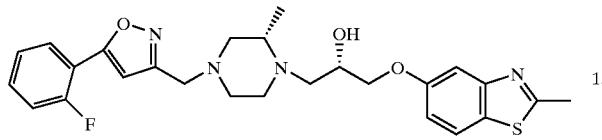

A. To a stirred solution of (2S)-methylpiperazine (40 mg, 0.40 mmol) in ethanol (5 mL) was added 3-chloromethyl-5-(2-fluorophenyl)isoxazole (42 mg, 0.20 mmol) and triethylamine (60µL, 0.43 mmol). The resulting mixture was stirred at 80° C. for 8 hours. It was then cooled, concentrated, and purified by preparative chromatography (1:9 methanol:methylene chloride) to yield 3-[((3S)-3-methylpiperazinyl)methyl]-5-(2-fluorophenyl)isoxazole (30 mg, M+1=276.14).

B. To a solution of 3-[((3S)-3-methylpiperazinyl)methyl]-5-(2-fluorophenyl)isoxazole (28 mg, 0.10 mmol) in tert-amylalcohol (5 mL) was added 5-[((2S)oxiran-2-yl)methoxy]-2-methylbenzothiazole (22 mg, 0.10 mmol). The reaction mixture was stirred at 95° C. for 1 day. It was then cooled, concentrated, and purified by preparative chromatography (1:19 methanol:methylene chloride) to afford (2S)-3-((2S)-4-{[5-(2-fluorophenyl)isoxazol-3-yl]methyl}-2-methylpiperazinyl)-1-(2-methylbenzothiazol-5-yloxy)propan-2-ol (19 mg, M+1=497.27).

EXAMPLE 5

Alternative Preparation of a Compound of Formula I

Preparation of a Compound of Formula I in which $R^1$, $R^2$, $R^3$, $R^4$, $R^5$, $R^6$, $R^7$, and $R^8$ are Hydrogen, T is Oxygen, $X^1$ is 3-Fluorophenyl, $X^2$ is 2-Methylbenzothiazol-5-yl, Y is 1,2,4-Oxadiazole, and $Z^1$ and $Z^2$ are Methylene

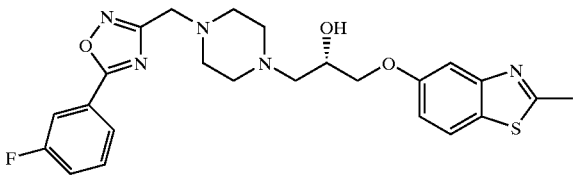

A. Preparation of 2-chloroacetamidoxime: Hydroxylamine hydrochloride (85 g, 1.22 mol) in water (250 mL) was treated with sodium carbonate (60 g, 0.58 mol), and the solution cooled to 0° C. Chloroacetonitrile (100 g, 1.32 mol) was added over 2 hours, and the reaction allowed to proceed for an additional 2 hours. The resultant slurry was filtered, washed with minimal cold $H_2O$, and dried to yield 2-chloroacetamidoxime (55.0 g, 42%).

B. 2-Chloroacetamidoxime (1 g, 9.2 mmol) in toluene (5 mL) at 0° C. under $N_2$ was treated with a solution of N,N-diisopropylethylamine (3.2 mL, 18.4 mmol) in toluene (5 mL). After 5 minutes a solution of 3-fluorobenzoyl chloride (1.49 g, 9.39 mmol) in toluene (5 mL) was added slowly over 20 minutes. The reaction was allowed to warm to room temperature overnight. The reaction was quenched with aqueous sodium bicarbonate (~100 mL) and extracted with ethyl acetate (3×100 mL). The combined organic extracts were dried over $MgSO_4$, filtered, and the solvent removed under vacuum to provide crude intermediate, which was used in the next step without further purification.

C.

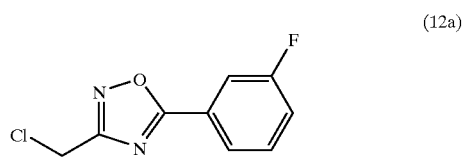

(12a)

The intermediate from the preceding step was dissolved in toluene (10 mL) and shaken on a J-Kem™. block at 110° C. for 60 hours. The reaction mixture was concentrated and flash chromatographed (98:2 to 90:10 hexanes-EtOAc) to give 3-(chloromethyl)-5-(3-fluorophenyl)-1,2,4-oxadiazole, a compound of formula (12a) (242 mg, 12%).

Formula I 3-(Chloromethyl)-5-(3-fluorophenyl)-1,2,4-oxadiazole (242 mg, 1.02 mmol) and (2S)-1-(2-methylbenzothiazol-5-yloxy)-3-piperazine-1-yl-propan-2-ol, a compound of formula (6) (309 mg, 1.0 mmol) in EtOH (8 mL) were treated with $Et_3N$ (0.5 mL, 3.57 mmol) and refluxed at 90° C. on a J-Kem™. block for 48 hours. The reaction product was concentrated and the product purified by flash chromatography (90:10 EtOAc-MeOH) to yield 3-(4-{[5-(3-fluorophenyl)(1,2,4-oxadiazol-3-yl)]methyl}piperazinyl)-1-(2-methylbenzothiazol-5-yloxy)propan-2-ol, a compound of Formula I.

D. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 5 above, but optionally replacing (2S)-1-(2-methylbenzothiazol-5-yloxy)-3-piperazine-1-yl-propan-2-ol with other compounds of formula (6), and optionally replacing 3-fluorobenzoyl chloride with other acid chlorides, other compounds of Formula I are prepared.

EXAMPLE 6

Alternative Preparation of a Compound of Formula I

Preparation of a Compound of Formula I in which $R^1$, $R^2$, $R^3$, $R^4$, $R^5$, $R^6$, $R^7$, and $R^8$ are Hydrogen, T is Oxygen, $X^1$ is 3-Fluorophenyl, $X^2$ is 2-Methylbenzothiazol-5-yl, Y is 1,2,4-Oxadiazole, and $Z^1$ and $Z^2$ are Methylene

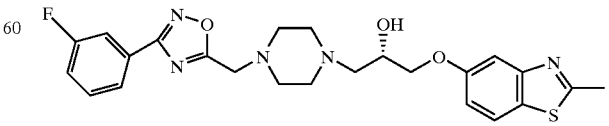

A. 3-Fluorobenzonitrile (3.2 mL, 30 mmol,) and hydroxylamine hydrochloride (4.6 g, 65.8 mmol) in ethanol (30 mL)

at 0° C. was treated with triethylamine (9.6 mL, 69 mmol). The solution was allowed to warm to room temperature, then shaken on a J-Kem™. block at 80° C. overnight. Upon cooling, ethyl acetate (40 mL) was added and the precipitate filtered and washed with ethyl acetate (~100 mL). The filtrate was washed with brine, dried (MgSO$_4$), filtered and concentrated. The crude product (3-fluorophenyl)(hydroxyimino)methylamine (4.96 g, 107%), a compound of formula (9), was used in the next step without further purification.

B (3-Fluorophenyl)(hydroxyimino)methylamine (4.96 g, 32.2 mmol) in dichloroethane (45 mL) was cooled to −20° C. and diisopropylethylamine (22.5 mL, 130 mmol) was added dropwise. The solution was stirred for 10 minutes at −20° C., then chloroacetylchloride (11.25 mL, 141 mmol) was added dropwise over ~5 min. The dark black solution was allowed to warm to room temperature, then shaken on a J-Kem™. block at 85° C. overnight. Upon cooling, the reaction mixture was diluted with dichloromethane (~200 mL), washed with water (×2) and brine, dried (MgSO$_4$), filtered and concentrated to a black oil. The oil was dissolved in 9:1 hexanes/ethyl acetate and filtered through a plug of SiO$_2$. The plug was washed first with 9:1 hexanes/ethyl acetate, then with ethyl acetate. The combined filtrates were concentrated and the product, 5-(chloromethyl)-3-(3-fluorophenyl)-1,2,4-oxadiazole, a compound of formula (11), was used in next step without further purification.

C. To 5-(chloromethyl)-3-(3-fluorophenyl)-1,2,4-oxadiazole (300 mg, 1.41 mmol) and (2S)-1-(2-methylbenzothiazol-5-yloxy)-3-piperazine-1-yl-propan-2-ol, a compound of formula (6) (291 mg, 0.94 mmol) in EtOH (20 mL, anhydrous) was added diisopropylethylamine (0.329 in, 1.89 mmol), and the reaction was shaken on a J-Kem™ block overnight at 90° C. Upon cooling to room temperature, the solution was concentrated to an oil and purified on an Isco™ Combi Flash Si 10×, using Redi Sep columns (10 g), eluting with ethyl acetate, then gradient to 4:1 ethyl acetate/methanol, to yield (2S)-3-(4-{[3-(3-fluorophenyl)(1,2,4-oxadiazol-5-yl)]methyl}piperazinyl)-1-(2-methylbenzothiazol-5-yloxy)propan-2-ol, a compound of Formula I, (136 mg, 30%).

D. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 6 above, but optionally replacing (2S)_1-(2-methylbenzothiazol-5-yloxy)-3-piperazine-1-yl-propan-2-ol with other compounds of formula (6), and optionally replacing 3-fluorobenzonitrile with other nitriles, other compounds of Formula I are prepared.

EXAMPLE 7

Preparation of a Compound of Formula I

Preparation of a Compound of Formula I in which $R^1$, $R^2$, $R^3$, $R^4$, $R^5$, $R^6$, $R^7$, and $R^8$ are Hydrogen, T is Oxygen, $X^1$ is 4-Trifluoromethylphenyl, $X^2$ is 2-Methylbenzothiazol-5-yl, Y is 1,3-Oxazole, and $Z^1$ and $Z^2$ are Methylene A. Preparation of a Compound of Formula (13)

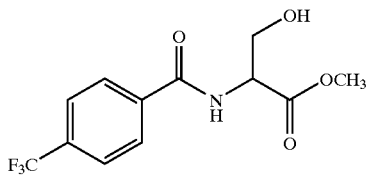

Methyl 2-amino-3-hydroxypropanoate hydrochloride (L-serine methyl ester hydrochloride, 1.71 g, 11 mmol) was stirred in dichloromethane (20 ml) at 0° C., and triethylamine (2.79 ml, 20 mmol) added, followed by dropwise addition of 4-trifluoromethylbenzoyl chloride (1.486 ml, 11 mmol). The mixture was stirred at 0° C. for 30 minutes, then partitioned between dichloromethane and water, dried over magnesium sulfate, and filtered. Solvent was removed from the filtrate under reduced pressure, and the residue was purified by column chromatography, to yield methyl 3-hydroxy-2-{[4-(trifluoromethyl)phenyl]carbonylamino}propanoate, a compound of formula (13).

B. Preparation of a Compound of Formula (14)

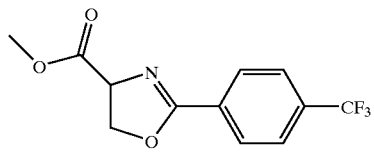

To a solution of methyl 3-hydroxy-2-{[4-(trifluoromethyl)phenyl]-carbonylamino}propanoate (2.57 g, 8.83 mmol) in tetrahydrofuran (30 ml) was added triphenylphosphine (2.55 g, 9.71 mmol). The mixture was cooled to 0° C., and diisopropylazodicarboxylate (1.91 ml, 9.71 mmol) was added slowly. The mixture was stirred at room temperature for 2 days. Solvent was removed from the filtrate under reduced pressure, and the residue was purified by column chromatography, to yield methyl 2-[4-(trifluoromethyl)phenyl]-1,3-oxazoline-4-carboxylate, a compound of formula (14).

C. Preparation of a Compound of Formula (15)

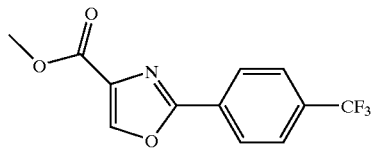

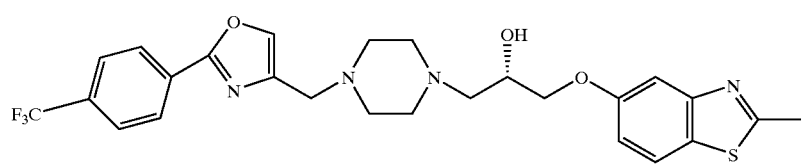

A solution of methyl 2-[4-(trifluoromethyl)phenyl]-1,3-oxazoline-4-carboxylate (1.33 g, 4.87 mmol) was stirred in toluene (60 ml) at 55° C. until all of the starting material was dissolved. 2,3-Dichloro-5,6-dicyano-1,4-benzoquinone (5.53 g, 24.365 mmol) was then added in portions, and the resulting solution was stirred at 75° C. for 36 hours. The solvent was evaporated under reduced pressure, and the residue was purified by column chromatography, to provide methyl 2-[4-(trifluoromethyl)phenyl]-1,3-oxazole-4-carboxylate, a compound of formula (15).

D. Preparation of a Compound of Formula (16)

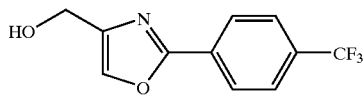

A solution of methyl 2-[4-(trifluoromethyl)phenyl]-1,3-oxazole-4-carboxylate (1.365 mmol) in tetrahydrofuran (20 ml) was cooled to 0° C., and lithium aluminum hydride in tetrahydrofuran (1.365 mmol) was added dropwise. The reaction mixture was stirred at 0° C. for 30 minutes, slowly quenched with water, followed by addition of ammonium chloride solution. The resulting mixture was filtered through celite, and washed with ethyl acetate. The filtrate was washed with brine, dried over sodium sulfate, and solvent removed under reduced pressure. The residue was purified by chromatography, to yield {2-[4-(trifluoromethyl)phenyl]-1,3-oxazol-4-yl}methan-1-ol, a compound of formula (16).

E. Preparation of a Compound of Formula I

A solution of {2-[4-(trifluoromethyl)phenyl]-1,3-oxazol-4-yl}methan-1-ol (0.19 g, 0.78 mmol) in tetrahydrofuran (15 ml) was cooled to 0° C., and triethylamine (0.33 ml, 2,34 mmol) was added, followed by methanesulfonyl chloride (0.12 ml, 1.56 mmol) dropwise. The mixture was stirred for 1 hour at 0° C., then water was added, and product was extracted with ethyl acetate. The organic layer was dried over sodium sulfate, and solvent removed from the filtrate under reduced pressure, to yield {2-[4-(trifluoromethyl)phenyl]-1,3-oxazol-4-yl}methyl methylsulfonate, the mesyl derivative of a compound of formula (15), The mesyl derivative (0.25 g, 0.78 mmol) was then mixed with tert-butyl piperazine carboxylate (0.29 g, 1.56 mmol) and triethylamine (0.33 ml, 2.34 mmol) in ethanol (20 ml), and the mixture refluxed for 2 hours. The solvent was removed under reduced pressure, and the residue partitioned between ethyl acetate and water. The organic layer was dried over sodium sulfate, and solvent removed from the filtrate, to provide tert-butyl 4-({2-[4-(trifluoromethyl)phenyl]-1,3-oxazol-4-yl}methyl)piperazinecarboxylate.

The BOC protecting group was then removed by treatment with 4N hydrochloric acid in dioxane at room temperature overnight, to provide 4-(piperazinylmethyl)-2-[4-(trifluoromethyl)phenyl]-1,3-oxazole, as its hydrochloride salt.

This compound (40 mg, 0.115 mmol) was dissolved in ethanol, and N,N-diisopropylethylamine (0.08 ml) and (2S)-1-(2-methylbenzothiazol-5-yloxy)-3-piperazine-1-yl-propan-2-ol, a compound of formula (6) (25 mg, 0.115 mmol), were added. The mixture was stirred at 85° C. for overnight, then solvent removed under reduced pressure, and the residue purified by preparative TLC, eluting with 5% methanol in dichloromethane, to provide (2S)-1-(2-methylbenzothiazol-5-yloxy)-3-[4-({2-[4-(trifluoromethyl)phenyl](1,3-oxazol-4-yl)}methyl)piperazinyl]propan-2-ol, a compound of Formula I.

F. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 7 above, but optionally replacing (2S)-1-(2-methylbenzothiazol-5-yloxy)-3-piperazine-1-yl-propan-2-ol with other compounds of formula (6), and optionally replacing 4-trifluoromethylbenzoyl chloride with other acid chlorides, other compounds of Formula I are prepared.

EXAMPLE 8

Preparation of a Compound of Formula I

Preparation of a Compound of Formula I in which $R^1$, $R^2$, $R^4$, $R^5$, $R^6$, $R^7$, and $R^8$ are Hydrogen, T is Oxygen, $X^1$ is 4-Fluoromethylphenyl, $X^2$ is 2-Cyclohexylbenzothiazol-5-yl, Y is N-Pyrazole, $Z^1$ is Ethylene, and $Z^2$ is Methylene

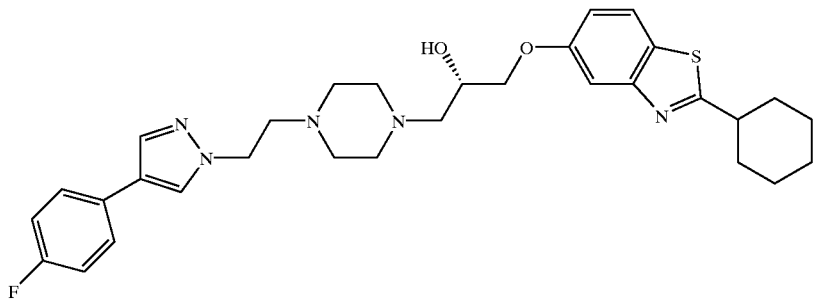

A To a solution of 4-fluoro-iodobenzene (2.22 g, 10 mmol) in ether at −78° C. was slowly added n-butyllithium (5 ml of 2.5M solution). The reaction mixture was stirred for 1 hour at −78° C., then tri-(n-butyl)tin chloride added, and the mixture stirred for a further 1 hour at −78° C. The mixture was allowed to warm to room temperature, then quenched with ammonium chloride solution, diluted with ether, washed with brine, dried over sodium sulfate, filtered, and solvent removed from the filtrate under reduced pressure, to provide 4-fluoro-(tri-n-butyl)tin-benzene, a compound of formula (17), as a liquid.

B. A mixture of 1-(2-chloroethyl)-4-iodopyrazole, a compound of formula (18), (2.0 g, 6.3 mmol) and 4-fluoro-(tri-n-butyl)tin-benzene (2.9 g, 7.6 mmol) in dry acetonitrile was stirred for 10 minutes under nitrogen. To this solution was added triphenylarsinc (385 mg, 1.26 mmol), copper iodide (120 mg, 0.63 mmol), and 10% palladium on carbon (250 mg), and the mixture heated at 80° C. for 48 hours. The mixture was cooled, filtered through celite, washed with dichloromethane, and the solvent removed from the filtrate under reduced pressure. The residue was flash chromatographed, eluting with dichloromethane, to provide 1-(2-chloroethyl)-4-(4-fluorophenyl)pyrazole, a compound of formula (19).

C. 1-(2-chloroethyl)-4-(4-fluorophenyl)pyrazole was then reacted with (2S)-1-(2-cyclohexylbenzothiazol-5-yloxy)-3-piperazine-1-yl-propan-2-ol, a compound of formula (6), as shown above to provide (2S)-3-(2-cyclohexylbenzothiazol-5-yloxy)-1-(4-{2-[4-(4-fluorophenyl)pyrazolyl]ethyl}piperazinyl)propan-2-ol.

D. Preparation of a Compound of Formula I, varying $R^1$, $R^2$, $R^3$ $R^4$, $R^5$, $R^6$, $R^7$ $R^8$, T, $X^1$, $X^2$, $Z^1$ and $Z^2$ Similarly, following the procedure of Example 8 above, but optionally replacing 4-fluoro-iodobenzene with other compounds of formula $X^1I$, and optionally replacing 1-(2-chloroethyl)-4-iodopyrazole with other optionally substituted pyrazoles, and optionally replacing 1-(2-cyclohexylbenzothiazol-5-yloxy)-3-piperazine-1-yl-propan-2-ol with other compounds of formula (6), other compounds of Formula I were prepared.

EXAMPLE 9

Preparation of a Compound of Formula I

Preparation of a Compound of Formula I in which $R^1$, $R^2$, $R^3$, $R^4$, $R^5$, $R^6$, $R^7$, and $R^8$ are Hydrogen, T is Oxygen, $X^1$ is 4-Trifluoromethylphenyl, $X^2$ is 2-Methylbenzothiazol-5-yl, Y is 5-Isoxazol-3-yl, and $Z^1$ and $Z^2$ are Methylene A. To a mixture of 1-(trifluoromethyl)-4-vinylbenzene (2.0 g, 11.27 mmol), a compound of formula (20) and ethyl 2-chloro-2-(hydroxyamino)acetate (2.11 g, 13.52 mmol), a compound of formula (21), in anhydrous THF was added a solution of triethylamine (3.0 ml) in tetrahydrofuran was added dropwise at room temperature. The mixture was stirred overnight under $N_2$. The white precipitate thus formed was filtered off, and washed twice with tetrahydrofuran (10 ml). The solvent was removed from the filtrate under reduced pressure, and the residue partitioned between water/ethyl acetate (20 ml:20 ml v/v), extracting three times with 20 ml of ethyl acetate. The combined organic layers were washed with aqueous ammonium chloride, and dried over $MgSO_4$, to provide ethyl 5-[4-(trifluoromethyl)phenyl]-4,5-dihydroisoxazole-3-carboxylate, a compound of formula (22).

B. A solution of ethyl 5-[4-(trifluoromethyl)phenyl]-4,5-dihydroisoxazole-3-carboxylate (3.3 g) was stirred in toluene (15 ml), and 2,3-dichloro-5,6-dicyano-1,4-benzoquinone (1.00 g) was then added in portions, followed by a portion of 3A molecular sieves, and the resulting mixture was stirred at 75° C. for 2 days. After cooling, ether was added and the mixture filtered through a layer anhydrous sodium sulfate. Solvent was evaporated under reduced pressure, and the residue was purified by column chromatography, to provide ethyl 5-[4-(trifluoromethyl)phenyl]isoxazole-3-carboxylate, a compound of formula (23).

C. Ethyl 5-[4-(trifluoromethyl)phenyl]isoxazole-3-carboxylate (130 mg) was dissolved in ethanol (10 ml), cooled to 0° C., and sodium borohydride (26 mg) was added in portions to the stirred solution. The mixture was stirred at room temperature for 4 hours, then excess water added. Solvent was evaporated under reduced pressure, and the residue was purified by preparative thin layer chromatography, eluting with 5% methanol/ethyl acetate, to provide {5-[4-(trifluoromethyl)phenyl]isoxazol-3-yl}methan-1-ol, a compound of formula (24).

D. {5-[4-(Trifluoromethyl)phenyl]isoxazol-3-yl}methan-1-ol (200 mg) was dissolved in dry dichloromethane (10 ml), and cooled to 0° C. The solution was stirred while adding a solution of thionyl chloride (2.74 ml) in dichloromethane (25 ml), then allowed to warm to room temperature and stirred overnight. Solvent was evaporated under reduced pressure, and the residue was purified by preparative thin layer chromatography, eluting with 30% ethyl acetate/hexane, to afford 3-(chloromethyl)-5-[4-(trifluoromethyl)phenyl]isoxazole, a compound of formula (25).

E. To a solution of (2S)-1-(2-methylbenzothiazol-5-yloxy)-3-piperazin-1-ylpropan-2-ol hydrochloride (50 mg) in t-butanol at room temperature was added triethylamine (60 μl), and the mixture was stirred at room temperature for 5 minutes. To this mixture was added 3-(chloromethyl)-5-[4-(trifluoromethyl)phenyl]isoxazole (26 mg), and the mixture was stirred at 100° C. overnight. The solvent was removed under reduced pressure, and the residue was dissolved in 1 ml of methanol, and purified by preparative thin layer

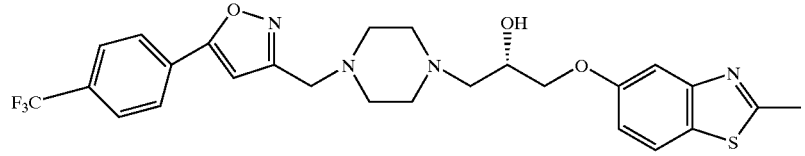

chromatography, eluting with 5% methanol/dichloromethane, to afford (2S)-1-(2-methylbenzothiazol-5-yloxy)-3-[4-({5-[4-(trifluoromethyl)phenyl]isoxazol-3-yl}methyl)piperazinyl]propan-2-ol, a compound of Formula I.

F. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 9 above, but optionally replacing 1-(trifluoromethyl)-4-vinylbenzene with other compounds of formula (20), and optionally replacing 1-(2-methylbenzothiazol-5-yloxy)-3-piperazin-1-ylpropan-2-ol hydrochloride with other compounds of formula (6), the following compounds of Formula I were prepared.

(2S)-3-[(2S)-2-methyl-4-({5-[4-chlorophenyl]isoxazol-3-yl}methyl)piperazinyl]-1-(2-methylbenzothiazol-5-yloxy)propan-2-ol;

(2S)-3-[(2S)-2-methyl-4-({5-[2-chlorophenyl]isoxazol-3-yl}methyl)piperazinyl]-1-(2-methylbenzothiazol-5-yloxy)propan-2-ol;

(2S)-3-[(2S)-2-methyl-4-({5-[4-(trifluoromethyl)phenyl]isoxazol-3-yl}methyl)piperazinyl]-1-(2-methylbenzothiazol-5-yloxy)propan-2-ol;

3-{(3R)-3-methyl-4-[(5-phenylisoxazol-3-yl)methyl]piperazinyl}(2S)-1-(2-methylbenzothiazol-5-yloxy)propan-2-ol;

(2S)-3-{(3S)-3-methyl-4-[(5-(3,4-dichlorophenyl)isoxazol-3-yl)methyl]piperazinyl}-1-(2-methylbenzothiazol-5-yloxy)propan-2-ol;

(2S)-3-((2S)-4-{[5-(3,4-dichlorophenyl)isoxazol-3-yl]methyl}-2-methylpiperazinyl)-1-(2-methylbenzothiazol-5-yloxy)propan-2-ol;

(2S)-3-{(3S)-3-methyl-4-[(5-(2-chlorophenyl)isoxazol-3-yl)methyl]piperazinyl}-1-(2-methylbenzothiazol-5-yloxy)propan-2-ol;

(2S)-3-{(3S)-3-methyl-4-[(5-(4-chlorophenyl)isoxazol-3-yl)methyl]piperazinyl}-1-(2-methylbenzothiazol-5-yloxy)propan-2ol;

3-{(3R)-3-methyl-4-[(5-methylisoxazol-3-yl)methyl]piperazinyl}(2S)-1-(2-methylbenzothiazol-5-yloxy)propan-2-ol;

(2S)-1-(2-methylbenzothiazol-5-yloxy)-3-(4-{[5-(4-methylphenyl)isoxazol-3-yl]methyl}piperazinyl)propan-2-ol;

(2S)-3-((3S)-3-methyl-4-{[5-(4-methylphenyl)isoxazol-3-yl]methyl}piperazinyl)-1-(2-methylbenzothiazol-5-yloxy)propan-2-ol;

(2S)-3-((3S)-3-methyl-4-{[5-(4-trifluoromethylphenyl)isoxazol-3-yl]methyl}-piperazinyl)-1-(2-methylbenzothiazol-5-yloxy)propan-2-ol;

(2S)-1-(2-methylbenzothiazol-5-yloxy)-3-(4-{[5-(4-phenylphenyl)isoxazol-3-yl]methyl}piperazinyl)propan-2-ol;

(2S)-3-((3S)-3-methyl-4-{[5-(4-phenylphenyl)isoxazol-3-yl]methyl}piperazinyl-1-(2-methylbenzothiazol-5-yloxy)propan-2-ol;

(2S)-3-((2S)-2-methyl-4-{[5-(4-methylphenyl)isoxazol-3-yl]methyl}piperazinyl)-1-(2-methylbenzothiazol-5-yloxy)propan-2-ol;

(2S)-3-((2S)-2-methyl-4-{[5-(4-phenylphenyl)isoxazol-3-yl]methyl}piperazinyl)-1-(2-methylbenzothiazol-5-yloxy)propan-2-ol;

(2S)-3-(4-{[5-(2,4-difluorophenyl)isoxazol-3-yl]methyl}piperazinyl)-1-(2-methylbenzothiazol-5-yloxy)propan-2-ol;

(2S)-3-((3 S)-4-{[5-(2,4-difluorophenyl)isoxazol-3-yl]methyl}-3-methylpiperazinyl)-1-(2-methylbenzothiazol-5-yloxy)propan-2-ol;

(2S)-1-(2-methylbenzothiazol-5-yloxy)-3-{4-[(5-naphthylisoxazol-3-yl)methyl]piperazinyl}propan-2-ol;

(2S)-3-{(3S)-3-methyl-4-[(5-naphthylisoxazol-3-yl)methyl]piperazinyl}-1-(2-methylbenzothiazol-5-yloxy)propan-2-ol;

(2S)-3-((3 S)-4-{[5-(2-fluorophenyl)isoxazol-3-yl]methyl}-3-methylpiperazinyl)-1-(2-methylbenzothiazol-5-yloxy)propan-2-ol;

(2S)-3-{(2S)-3-methyl-4-[(5-naphthylisoxazol-3-yl)methyl]piperazinyl}-1-(2-methylbenzothiazol-5-yloxy)propan-2-ol;

(2S)-3-{(2S)-3-methyl-4-[(5-(2-fluorophenyl)isoxazol-3-yl)methyl]piperazinyl}-1-(2-methylbenzothiazol-5-yloxy)propan-2-ol;

(2S)-3-{4-[(5-methyl(1,2-isoxazol-3-yl))methyl]piperazinyl}-1-(2-methylbenzothiazol-5-yloxy)propan-2-ol;

(2S)-3-{4-[(5-(2-thien-yl)(1,2-isoxazol-3-yl))methyl]piperazinyl}-1-(2-methylbenzothiazol-5-yloxy)propan-2-ol;

(2S)-3-[(2S)-2-methyl-4-({5-[4-phenylphenyl](1,2,4-oxadiazol-3-yl)}methyl)piperazinyl]-1-(2-methylbenzothiazol-5-yloxy)propan-2-ol; and (2S)-3-[(2S)-2-methyl-4-({5-[4-(trifluoromethyl)phenyl](1,2,4-oxadiazol-3-yl)}methyl)piperazinyl]-1-(2-methylbenzothiazol-5-yloxy)propan-2-ol.

G. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 9 above, but optionally replacing 1-(trifluoromethyl)-4-vinylbenzene with other compounds of formula (20), and optionally replacing (2S)-1-(2-methylbenzothiazol-5-yloxy)-3-piperazin-1-ylpropan-2-ol hydrochloride with other compounds of formula (6), other compounds of Formula I are prepared.

EXAMPLE 10

Using the procedures of Examples 1–9 above, the following compounds of Formula I were prepared:

| | |
|---|---|
| 1 | (2S)-3-[(2S)-2-methyl-4-({5-[4-(trifluoromethyl)phenyl](1,2,4-oxadiazol-3-yl)}methyl)piperazinyl]-1-(2-methylbenzothiazol-5-yloxy)propan-2-ol |
| 2 | 1-(2-methylbenzothiazol-5-yloxy)-3-[4-({5-[4-(trifluoromethyl)phenyl](1,2,4-oxadiazol-3-yl)}methyl)piperazinyl]propan-2-ol( |
| 3 | (2S)-1-(2-methylbenzothiazol-5-yloxy)-3-[4-({5-[4-(trifluoromethyl)phenyl](1,2,4-oxadiazol-3-yl)}methyl)piperazinyl]propan-2-ol |
| 4 | 2S)-3-(2-fluorophenoxy)-1-[4-({5-[4-(trifluoromethyl)phenyl](1,2,4-oxadiazol-3-yl)}methyl)piperazinyl]propan-2-ol |
| 5 | 3-(2-methoxyphenoxy)-1-[4-({5-[4-(trifluoromethyl)phenyl](1,2,4-oxadiazol-3-yl)}methyl)piperazinyl]propan-2-ol |
| 6 | (2S)-1-(2-methylbenzothiazol-5-yloxy)-3-{4-[5-(trifluoromethyl)(2-pyridyl)]piperazinyl}propan-2-ol |
| 7 | (2S)-1-(2-methylbenzothiazol-5-yloxy)-3-{4-[(5-phenyl(1,2,4-oxadiazol-3-yl))methyl]piperazinyl}propan-2-ol |
| 8 | (2S)-1-(2-methylbenzothiazol-5-yloxy)-3-[4-({3-[4-(trifluoromethyl)phenyl](1,2,4-oxadiazol-5-yl)}methyl)piperazinyl]propan-2-ol |
| 9 | (2S)-1-(2-methylbenzothiazol-5-yloxy)-3-{4-[(5-naphthyl(1,2,4-oxadiazol-3-yl))methyl]piperazinyl}propan-2-ol |
| 10 | (2S)-1-(2-methylbenzothiazol-5-yloxy)-3-{4-[(5-phenyl(1,2,4-oxadiazol-3-yl))methyl]piperazinyl}propan-2-ol |
| 11 | (2S)-1-(2-methylbenzothiazol-5-yloxy)-3-(4-{[5-(3-methylphenyl)(1,2,4-oxadiazol-3-yl)]methyl}piperazinyl)propan-2-ol |
| 12 | (2S)-1-(2-methylbenzothiazol-5-yloxy)-3-[4-({3-[4-(trifluoromethyl)phenyl](1,2,4-oxadiazol-5-yl)}methyl)piperazinyl]propan-2-ol |
| 13 | (2S)-3-(4-{[5-(3-chlorophenyl)(1,2,4-oxadiazol-3-yl)]methyl}piperazinyl)-1-(2-methylbenzothiazol-6-yloxy)propan-2-ol |

-continued

| | |
|---|---|
| 14 | (2S)-3-{4-[(5-cyclopentyl(1,2,4-oxadiazol-3-yl))methyl]piperazinyl}-1-(2-methylbenzothiazol-6-yloxy)propan-2-oll |
| 15 | (2S)-3-(4-{[5-(3-fluorophenyl)(1,2,4-oxadiazol-3-yl)]methyl}piperazinyl)-1-(2-methylbenzothiazol-6-yloxy)propan-2-ol |
| 16 | 3-(4-{[5-(4-cyanophenyl)(1,2,4-oxadiazol-3-yl)]methyl}piperazinyl)-1-(2-methylbenzothiazol-5-yloxy)propan-2-ol |
| 17 | 3-(4-{[5-(3-cyanophenyl)(1,2,4-oxadiazol-3-yl)]methyl}piperazinyl)-1-(2-methylbenzothiazol-5-yloxy)propan-2-ol |
| 18 | (2S)-1-(2-methylbenzothiazol-5-yloxy)-3-(4-{[3-(4-methylphenyl)(1,2,4-oxadiazol-5-yl)]methyl}piperazinyl)propan-2-ol |
| 19 | (2S)-1-(2-methylbenzothiazol-5-yloxy)-3-(4-{[3-(3-phenylphenyl)(1,2,4-oxadiazol-5-yl)]methyl}piperazinyl)propan-2-ol |
| 20 | (2S)-3-(4-{[3-(3-fluorophenyl)(1,2,4-oxadiazol-5-yl)]methyl}piperazinyl)-1-(2-methylbenzothiazol-5-yloxy)propan-2-ol |
| 21 | (2S)-1-(2-methylbenzothiazol-5-yloxy)-3-[4-({3-[2-(trifluoromethyl)phenyl](1,2,4-oxadiazol-5-yl)}methyl)piperazinyl]propan-2-ol |
| 22 | (2S)-3-{4-[(3-cyclohexyl(1,2,4-oxadiazol-5-yl))methyl]piperazinyl}-1-(2-methylbenzothiazol-5-yloxy)propan-2-ol |
| 23 | (2S)-1-(4-{[3-(3,4-dichlorophenyl)(1,2,4-oxadiazol-5-yl)]methyl}piperazinyl)-3-(2-methylbenzothiazol-5-yloxy)propan-2-ol |
| 24 | (2S)-1-(2-methylbenzothiazol-5-yloxy)-3-[4-({3-[4-(trifluoromethoxy)phenyl](1,2,4-oxadiazol-5-yl)}methyl)piperazinyl]propan-2-ol |
| 25 | (2S)-3-(4-{[3-(4-fluorophenyl)(1,2,4-oxadiazol-5-yl)]methyl}piperazinyl)-1-(2-methylbenzothiazol-5-yloxy)propan-2-ol |
| 26 | (2S)-3-[4-({3-[4-(tert-butyl)phenyl](1,2,4-oxadiazol-5-yl)}methyl)piperazinyl]-1-(2-methylbenzothiazol-5-yloxy)propan-2-ol |
| 27 | (2S)-1-(2-methylbenzothiazol-5-yloxy)-3-[4-({3-[4-(methylethyl)phenyl](1,2,4-oxadiazol-5-yl)}methyl)piperazinyl]propan-2-ol |
| 28 | (2S)-1-(2-methylbenzothiazol-5-yloxy)-3-(4-{[3-(4-phenylphenyl)(1,2,4-oxadiazol-5-yl)]methyl}piperazinyl)propan-2-ol |
| 29 | 3-(4-{[3-(4-cyanophenyl)(1,2,4-oxadiazol-5-yl)]methyl}piperazinyl)-1-(2-methylbenzothiazol-5-yloxy)propan-2-ol |
| 30 | (2S)-1-(2-methylbenzothiazol-5-yloxy)-3-(4-{[3-(3-methylphenyl)(1,2,4-oxadiazol-5-yl)]methyl}piperazinyl)propan-2-ol |
| 31 | (2S)-3-(4-{[3-(3-chlorophenyl)(1,2,4-oxadiazol-5-yl)]methyl}piperazinyl)-1-(2-methylbenzothiazol-5-yloxy)propan-2-ol |
| 32 | (2S)-3-{4-[(3-cyclopentyl(1,2,4-oxadiazol-5-yl))methyl]piperazinyl}-1-(2-methylbenzothiazol-5-yloxy)propan-2-ol |
| 33 | (2S)-1-(2-methylbenzothiazol-5-yloxy)-3-(4-[(3-naphthyl(1,2,4-oxadiazol-5-yl))methyl]piperazinyl}propan-2-ol |
| 34 | (2S)-1-(2-methylbenzothiazol-5-yloxy)-3-[4-({5-[4-(trifluoromethoxy)phenyl](1,2,4-oxadiazol-3-yl)}methyl)piperazinyl]propan-2-ol |
| 35 | (2S)-3-(4-{[5-(4-chlorophenyl)(1,2,4-oxadiazol-3-yl)]methyl}piperazinyl)-1-(2-methylbenzothiazol-5-yloxy)propan-2-ol |
| 36 | (2S)-1-(2-methylbenzothiazol-5-yloxy)-3-(4-{[5-(4-methylphenyl)(1,2,4-oxadiazol-3-yl)]methyl}piperazinyl)propan-2-ol |
| 37 | (2S)-3-[4-({3-[3-chloro-4-(trifluoromethyl)phenyl](1,2,4-oxadiazol-5-yl)}methyl)piperazinyl]-1-(2-methylbenzothiazol-5-yloxy)propan-2-ol |
| 38 | (2S)-3-(4-{[5-(4-fluorophenyl)(1,2,4-oxadiazol-3-yl)]methyl}piperazinyl)-1-(2-methylbenzothiazol-6-yloxy)propan-2-ol |
| 39 | (2S)-3-(4-{[5-(3,4-dichlorophenyl)(1,2,4-oxadiazol-3-yl)]methyl}piperazinyl)-1-(2-methylbenzothiazol-6-yloxy)propan-2-ol |
| 40 | (2S)-3-(4-{[5-(2-chlorophenyl)isoxazol-3-yl]methyl}piperazinyl)-1-(2-methylbenzothiazol-5-yloxy)propan-2-ol |
| 41 | (2S)-3-(4-{[5-(4-chlorophenyl)isoxazol-3-yl]methyl}piperazinyl)-1-(2-methylbenzothiazol-5-yloxy)propan-2-ol |
| 42 | (2S)-3-(4-{[3-(4-methoxyphenyl)isoxazol-5-yl]methyl}piperazinyl)-1-(2-methylbenzothiazol-5-yloxy)propan-2-ol |
| 43 | (2S)-1-(2-methylbenzothiazol-5-yloxy)-3-[4-({5-[4-(trifluoromethyl)phenyl](4,5-dihydroisoxazol-3-yl)}methyl)piperazinyl]propan-2-ol |
| 44 | 3-(4-{[3-(4-sulfonamidophenyl)(1,2,4-oxadiazol-5-yl)]methyl}piperazinyl)-1-(2-methylbenzothiazol-5-yloxy)propan-2-ol |
| 45 | 3-(4-([3-(3-cyanophenyl)(1,2,4-oxadiazol-5-yl)]methyl}piperazinyl)-1-(2-methylbenzothiazol-5-yloxy)propan-2-ol |
| 46 | 3-(4-{[3-(4-(methyl 2,2-dimethylacetate)phenyl)(1,2,4-oxadiazol-5-yl)]methyl}piperazinyl)-1-(2-methylbenzothiazol-5-yloxy)propan-2-ol |
| 47 | ethyl 2-{4-[5-({4-[(2S)-2-hydroxy-3-(2-methylbenzothiazol-5-yloxy))propyl]piperazinyl}methyl)(1,2,4-oxadiazol-3-yl)]phenoxy}-2-methylpropanoate |
| 48 | ethyl 2-{4-[5-({4-[(2S)-2-hydroxy-3-(2-methyl(5,6-dihydrobenzothiazol-5-yloxy))propyl]piperazinyl}methyl)(1,2,4-oxadiazol-3-yl)]phenoxy}-2-methylpropanoate |
| 49 | 2-{4-[5-({4-[(2S)-2-hydroxy-3-(2-methylbenzothiazol-5-yloxy)propyl]piperazinyl}methyl)(1,2,4-oxadiazol-3-yl)]phenoxy}-2-methylpropanoic acid |
| 50 | 1-[(2S)-2-hydroxy-3-(2-methylbenzothiazol-5-yloxy)propyl]-4-({5-[4-(trifluoromethyl)phenyl](1,2,4-oxadiazol-3-yl)}methyl)piperazine-2-carboxamide |
| 51 | (2S)-1-(2-methylbenzothiazol-5-yloxy))-3-{4-[(5-phenylisoxazol-3-yl)methyl]piperazinyl}propan-2-ol |
| 52 | (2S)-1-(2-methylbenzothiazol-5-yloxy))-3-[4-({5-[4-(trifluoromethyl)phenyl] isoxazol-3-yl}methyl)piperazinyl]propan-2-ol |

-continued

| | |
|---|---|
| 53 | 1-(2-methylbenzothiazol-5-yloxy)-3-{4-[(1-phenylpyrrol-3-yl)methyl] piperazinyl}propan-2-ol |
| 54 | (2S)-1-[2-(2-chlorophenyl)benzoxazol-5-yloxy]-3-[4-({5-[4-(trifluoromethyl)phenyl](1,2,4-oxadiazol-3-yl)}methyl)piperazinyl]propan-2-ol |
| 55 | (2S)-1-(2-ethylbenzothiazol-5-yloxy)-3-[4-({5-[4-(trifluoromethyl)phenyl](1,2,4-oxadiazol-3-yl)}methyl)piperazinyl]propan-2-ol |
| 56 | (2S)-1-(2-propylbenzothiazol-5-yloxy)-3-[4-({5-[4-(trifluoromethyl)phenyl](1,2,4-oxadiazol-3-yl)}methyl)piperazinyl]propan-2-ol |
| 57 | (2S)-3-[4-({5-[4-(trifluoromethyl)phenyl](1,2,4-oxadiazol-3-yl)}methyl)piperazinyl]-1-{2-[2-(trifluoromethyl)phenyl]benzoxazol-5-yloxy}propan-2-ol |
| 58 | (2S)-3-[4-({5-[4-(trifluoromethyl)phenyl](1,2,4-oxadiazol-3-yl)}methyl)piperazinyl]-1-{2-[3-(trifluoromethyl)phenyl]benzoxazol-5-yloxy}propan-2-ol |
| 59 | (2S)-1-(2-phenylbenzothiazol-5-yloxy)-3-{4-[2-(4-phenylpyrazolyl)ethyl]piperazinyl}propan-2-ol |
| 60 | (2S)-3-(4-{2-[4-(4-fluorophenyl)pyrazolyl]ethyl}piperazinyl)-1-(2-phenylbenzothiazol-5-yloxy)propan-2-ol |
| 61 | (2S)-1-(2-phenylbenzothiazol-5-yloxy)-3-[4-(2-{4-[4-(trifluoromethyl)phenyl]pyrazolyl}ethyl)piperazinyl]propan-2-ol |
| 62 | (2S)-1-(2-ethylbenzothiazol-5-yloxy)-3-{4-[2-(4-phenylpyrazolyl)ethyl]piperazinyl}propan-2-ol |
| 63 | (2S)-1-(2-ethylbenzothiazol-5-yloxy)-3-(4-{2-[4-(4-fluorophenyl)pyrazolyl]ethyl}piperazinyl)propan-2-ol |
| 64 | (2S)-1-(2-ethylbenzothiazol-5-yloxy)-3-[4-(2-{4-[4-(trifluoromethyl)phenyl]pyrazolyl}ethyl)piperazinyl]propan-2-ol |
| 65 | (2S)-1-(2-methylbenzothiazol-5-yloxy)-3-{4-[2-(4-phenylpyrazolyl)ethyl]piperazinyl}propan-2-ol |
| 66 | (2S)-3-(4-{2-[4-(4-fluorophenyl)pyrazolyl]ethyl}piperazinyl)-1-(2-methylbenzothiazol-5-yloxy)propan-2-ol |
| 67 | (2S)-1-(2-methylbenzothiazol-5-yloxy)-3-[4-(2-{4-[4-(trifluoromethyl)phenyl]pyrazolyl}ethyl)piperazinyl]propan-2-ol |
| 68 | (2S)-3-{4-[2-(4-phenylpyrazolyl)ethyl]piperazinyl}-1-(2-propylbenzothiazol-5-yloxy)propan-2-ol |
| 69 | (2S)-3-(4-{2-[4-(4-fluorophenyl)pyrazolyl]ethyl}piperazinyl)-1-(2-propylbenzothiazol-5-yloxy)propan-2-ol |
| 70 | (2S)-1-(2-propylbenzothiazol-5-yloxy)-3-[4-(2-{4-[4-(trifluoromethyl)phenyl]pyrazolyl}ethyl)piperazinyl]propan-2-ol |
| 71 | 3-[2-(3-fluorophenyl)benzoxazol-5-yloxy]-1-[4-({2-[4-(trifluoromethyl)phenyl](1,3-oxazol-4-yl)}methyl)piperazinyl]propan-2-ol |
| 72 | 3-[2-(4-fluorophenyl)benzoxazol-5-yloxy]-1-[4-({2-[4-(trifluoromethyl)phenyl](1,3-oxazol-4-yl)}methyl)piperazinyl]propan-2-ol |
| 73 | 1-(2-methylbenzothiazol-5-yloxy)-3-[4-({2-[4-(trifluoromethyl)phenyl](1,3-oxazol-4-yl)}methyl)piperazinyl]propan-2-ol |
| 74 | (2S)-3-(4-{[(4S)-2-(4-fluorophenyl)(1,3-oxazolin-4-yl)]methyl}piperazinyl)-1-(2-methylbenzothiazol-5-yloxy)propan-2-ol |
| 75 | (2S)-1-(2-methylbenzothiazol-5-yloxy)-3-{4-[(3-phenylisoxazol-5-yl)methyl]piperazinyl}propan-2-ol |
| 76 | (2S)-1-(2-methylbenzothiazol-5-yloxy)-3-{4-[(3-methyl-5-phenylisoxazol-4-yl)methyl]piperazinyl}propan-2-ol |
| 77 | (2S)-3-(4-{[5-(3,4-dichlorophenyl)isoxazol-3-yl]methyl}piperazinyl)-1-(2-methylbenzothiazol-5-yloxy)propan-2-ol |
| 78 | 3-[2-(2-chlorophenyl)benzoxazol-5-yloxy]-1-[4-({2-[4-(trifluoromethyl)phenyl](1,3-oxazol-4-yl)}methyl)piperazinyl]propan-2-ol |
| 79 | (2S)-3-(4-{[3-(4-fluorophenyl)isoxazol-5-yl]methyl}piperazinyl)-1-(2-methylbenzothiazol-5-yloxy)propan-2-ol |
| 80 | (2S)-1-[2-(2-chlorophenyl)benzoxazol-5-yloxy]-1-(4-{[3-(4-fluorophenyl)isoxazol-5-yl]methyl}piperazinyl)propan-2-ol |
| 81 | (2S)-3-[2-(3-fluorophenyl)benzoxazol-5-yloxy]-1-(4-{[3-(4-fluorophenyl)isoxazol-5-yl]methyl}piperazinyl)propan-2-ol |
| 82 | (2S)-3-[2-(4-fluorophenyl)benzoxazol-5-yloxy]-1-(4-{[3-(4-fluorophenyl)isoxazol-5-yl]methyl}piperazinyl)propan-2-ol |
| 83 | (2S)-1-(2-cyclohexylbenzothiazol-5-yloxy)-3-{4-[2-(4-phenylpyrazolyl)ethyl]piperazinyl}propan-2-ol |
| 84 | (2S)-1-(2-cyclohexylbenzothiazol-5-yloxy)-3-(4-{2-[4-(4-fluorophenyl)pyrazolyl]ethyl}piperazinyl)propan-2-ol |
| 85 | (2S)-1-(2-cyclohexylbenzothiazol-5-yloxy)-3-[4-(2-{4-[4-(trifluoromethyl)phenyl]pyrazolyl}ethyl)piperazinyl]propan-2-ol |
| 86 | (2S)-3-{4-[2-(2,5-dimethylpyrrolyl)ethyl]piperazinyl}-13-(2-methylbenzothiazol-5-yloxy)propan-2-ol |
| 87 | (2S)-13-(2-methylbenzothiazol-5-yloxy)-31-{4-[(5-methyl-2-phenyl(1,2,3-triazol-4-yl))methyl]piperazinyl}propan-2-ol |
| 88 | (2S)-13-(2-methylbenzothiazol-5-yloxy)-31-{4-[(3-(2-thienyl)(1,2,4-oxadiazol-5-yl))methyl]piperazinyl}propan-2-ol |
| 89 | (2S)-1-(2-methylbenzothiazol-5-yloxy)-31-[4-({5-[2-(trifluoromethyl)phenyl]isoxazol-3-yl}methyl)piperazinyl]propan-2-ol |
| 90 | (2S)-1-[2-(4-chlorophenyl)benzoxazol-5-yloxy]-3-(4-{[3-(2-methoxyphenyl)isoxazol-5-yl]methyl}piperazinyl)propan-2-ol |
| 91 | (2S)-3-(4-{[3-(2,4-dimethoxyphenyl)isoxazol-5-yl]methyl}piperazinyl)-3-[2-(4-chlorophenyl)benzoxazol-5-yloxy]propan-2-ol |

| | -continued |
|---|---|
| 92 | (2S)-3-(4-{[3-(2-methoxyphenyl)isoxazol-5-yl]methyl}piperazinyl)-1-(2-methylbenzothiazol-5-yloxy)propan-2-ol |
| 93 | (2S)-3-(4-{[3-(2,4-dimethoxyphenyl)isoxazol-5-yl]methyl}piperazinyl)-1-(2-methylbenzothiazol-5-yloxy)propan-2-ol |
| 94 | (2S)-3-[2-(3-fluorophenyl)benzoxazol-5-yloxy]-1-(4-{[3-(2-methoxyphenyl)isoxazol-5-yl]methyl}piperazinyl)propan-2-ol |
| 95 | (2S)-1-(4-{[3-(2,4-dimethoxyphenyl)isoxazol-5-yl]methyl}piperazinyl)-3-[2-(3-fluorophenyl)benzoxazol-5-yloxy]propan-2-ol |
| 96 | (2S)-3-[2-(4-fluorophenyl)benzoxazol-5-yloxy]-1-(4-{[3-(2-methoxyphenyl)isoxazol-5-yl]methyl}piperazinyl)propan-2-ol |
| 97 | (2S)-3-(4-{[3-(2,4-dimethoxyphenyl)isoxazol-5-yl]methyl}piperazinyl)-1-[2-(4-fluorophenyl)benzoxazol-5-yloxy]propan-2-ol |
| 98 | (2S)-1-[2-(4-chlorophenyl)benzoxazol-5-yloxy]-3-(4-{[3-(2-chlorophenyl)isoxazol-5-yl]methyl}piperazinyl)propan-2-ol |
| 99 | (2S)-3-(4-{[3-(2,6-dichlorophenyl)isoxazol-5-yl]methyl}piperazinyl)-1-[2-(4-chlorophenyl)benzoxazol-5-yloxy]propan-2-ol |
| 100 | (2S)-3-(4-{[3-(2-chlorophenyl)isoxazol-5-yl]methyl}piperazinyl)-1-(2-phenylbenzothiazol-5-yloxy)propan-2-ol |
| 101 | (2S)-3-(4-{[3-(2,6-dichlorophenyl)isoxazol-5-yl]methyl}piperazinyl)-1-(2-phenylbenzothiazol-5-yloxy)propan-2-ol |
| 102 | (2S)-3-(4-{[3-(2-methoxyphenyl)isoxazol-5-yl]methyl}piperazinyl)-1-(2-phenylbenzothiazol-5-yloxy)propan-2-ol |
| 103 | (2S)-3-(4-{[3-(2,4-dimethoxyphenyl)isoxazol-5-yl]methyl}piperazinyl)-1-(2-phenylbenzothiazol-5-yloxy)propan-2-ol |
| 104 | (2S)-3-(4-{[3-(2-chlorophenyl)isoxazol-5-yl]methyl}piperazinyl)-1-(2-methylbenzothiazol-5-yloxy)propan-2-ol |
| 105 | (2S)-3-(4-{[3-(2,6-dichlorophenyl)isoxazol-5-yl]methyl}piperazinyl)-1-(2-methylbenzothiazol-5-yloxy)propan-2-ol |
| 106 | (2S)-3-(4-{[3-(2-chlorophenyl)isoxazol-5-yl]methyl}piperazinyl)-1-[2-(3-fluorophenyl)benzoxazol-5-yloxy]propan-2-ol |
| 107 | (2S)-3(4-{[3-(2,6-dichlorophenyl)isoxazol-5-yl]methyl}piperazinyl)-1-[2-(3-fluorophenyl)benzoxazol-5-yloxy]propan-2-ol |
| 108 | (2S)-3-(4-{[3-(2-chlorophenyl)isoxazol-5-yl]methyl}piperazinyl)-1-[2-(4-fluorophenyl)benzoxazol-5-yloxy]propan-2-ol |
| 109 | (2S)-3-(4-{[3-(2,6-dichlorophenyl)isoxazol-5-yl]methyl}piperazinyl)-1-[2-(4-fluorophenyl)benzoxazol-5-yloxy]propan-2-ol |
| 110 | (2S)-1-[2-(2-phenyl(1,3-oxazol-4-yl))ethoxy]-3-[4-({5-[4-(trifluoromethyl)phenyl](1,2,4-oxadiazol-3-yl)}methyl)piperazinyl]propan-2-ol |
| 111 | (2S)-1-[2-(4-chlorophenyl)benzoxazol-5-yloxy]-3-{4-[(5-methyl-2-phenyl(1,2,3-triazol-4-yl))methyl]piperazinyl}propan-2-ol |
| 112 | (2S)-1-[2-(4-chlorophenyl)benzoxazol-5-yloxy]-3-{4-[(3-(2-thienyl)(1,2,4-oxadiazol-5-yl))methyl]piperazinyl}propan-2-ol |
| 113 | (2S)-3-{4-[(5-methyl-2-phenyl(1,2,3-triazol-4-yl))methyl]piperazinyl}-1-(2-phenylbenzothiazol-5-yloxy)propan-2-ol |
| 114 | (2S)-1-(2-phenylbenzothiazol-5-yloxy)-3-{4-[(3-(2-thienyl)(1,2,4-oxadiazol-5-yl))methyl]piperazinyl}propan-2-ol |
| 115 | (2S)-3-(4-{[3-(4-hydroxyphenyl)isoxazol-5-yl]methyl}piperazinyl)-1-(2-methylbenzothiazol-5-yloxy)propan-2-ol |

EXAMPLE 11

Preparation of a Compound of Formula I

Preparation of a Compound of Formula I in which $R^1$, $R^2$, $R^3$, $R^4$, $R^5$, $R^6$, $R^7$, and $R^8$ are Hydrogen, T is Oxygen, $X^1$ is 2,3-Dichlorophenyl, $X^2$ is 2-Methylbenzothiazol-5-yl, Y is 3-Isoxazol-5-yl, and $Z^1$ and $Z^2$ are Methylene A. Preparation of a Compound of Formula (26) in which $R^1$, $R^2$, $R^3$, $R^4$, $R^5$, $R^6$, $R^7$, and $R^8$ are Hydrogen, $X^2$ is 2-Methylbenzothiazol-5-yl, and $Z^1$ and $Z^2$ are Methylene

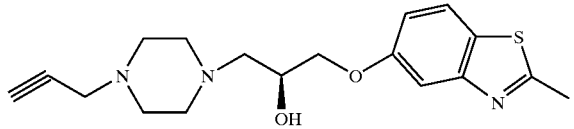

To a solution of (2S)-1-(2-methylbenzothiazol-5-yloxy)-3-piperazinylpropan-2-ol (800 mg, 2.6 mmol) in acetone (20 ml) was added propargyl bromide (80% solution, 0.290 ml, 2.6 mmol) and potassium carbonate (720 mg, 5.2 mmol). The solution was heated to reflux and stirred for 5 hours. Thin layer chromatography (10:1 dichloromethane:methanol) showed formation of product. The solution was cooled and filtered. The filtrate was concentrated and purified by preparative chromatography (dichloromethane:methanol) to yield (2S)-1-(2-methylbenzothiazol-5-yloxy)-3-(4-prop-2-ynylpiperazinyl)propan-2-ol (500 mg, M+1=346.2).

B. Preparation of a Compound of Formula I

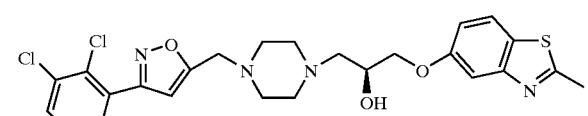

To a solution of 2,3 dichlorobenzaldehyde oxime (136 mg, 0.725 mmol) in 1 ml of dichloromethane was added aqueous sodium hypochlorite solution (>4%, 1.35 ml, 0.725 mmol). The reaction was sealed in a reaction vessel with a stirbar. The vessel was subjected to microwave under the following conditions: temperature=60° C., time=240(s), high absorbance, fixed hold time=on, pre-stir=10(s). After 4 minutes (2S)-1-(2-methylbenzothiazol-5-yloxy)-3-(4-prop-2-ynylpiperazinyl)propan-2-ol (50 mg, 0.145 mmol) in 1 ml of dichloromethane was added, followed by triethylamine (0.022 ml, 0.145 mmol). The reaction vessel was again subjected to microwave under the following conditions: temperature=110° C., time=240(s), high absorbance, fixed hold time=on, pre-stir=10(s). After 4 minutes, thin layer chromatography (10:1 dichloromethane:methanol) showed consumption of starting material and product formation. The solution was evaporated under reduced pressure and purified by preparative thin layer chromatography (10:1 dichloromethane:methanol) followed by HPLC to yield (2S)-3-(4-{[3-(2,3-dichlorophenyl)isoxazol-5-yl]methyl}piperazinyl)-1-(2-methylbenzothiazol-5-yloxy)propan-2-ol (20) (3.2 mg, M+1=533.21)

C. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 11 above, but optionally replacing (2S)-1-(2-methylbenzothiazol-5-yloxy)-3-(4-prop-2-ynylpiperazinyl)propan-2-ol with other compounds of formula (26), and optionally replacing 2,3 dichlorobenzaldehyde oxime with other oximes of formula $X^1$—CH=NOH, the following compounds of Formula I were prepared:

(2S)-3-{(3S)-3-methyl-4-[(3-(4-methoxyphenyl)isoxazol-5-yl)methyl]piperazinyl}-1-(2-methylbenzothiazol-5-yloxy)propan-2-ol;
(2S)-3-{(3S)-3-methyl-4-[(3-phenylisoxazol-5-yl)methyl] piperazinyl}-1-(2-methylbenzothiazol-5-yloxy)propan-2-ol;
(2S)-3-{(2S)-2-methyl-4-[(3-phenylisoxazol-5-yl)methyl] piperazinyl}-1-(2-methylbenzothiazol-5-yloxy)propan-2-ol;
(2S)-3-{(2S)-2-methyl-4-[(3-(4-methoxyphenyl)isoxazol-5-yl)methyl]piperazinyl}-1-(2-methylbenzothiazol-5-yloxy)propan-2-ol;
3-{(2S)-2-methyl-4-[(5-phenylisoxazol-3-yl)methyl]piperazinyl}(2S)-1-(2-methylbenzothiazol-5-yloxy)propan-2-ol;
(2S)-3-[4-({3-[3-chloro-5-(trifluoromethyl)(2-pyridyl)] isoxazol-5-yl}ethyl)piperazinyl]-1-(2-methylbenzothiazol-5-yloxy)propan-2-ol;
(2S)-3-[(3S)-4-({3-[3-chloro-5-(trifluoromethyl)(2-pyridyl)]isoxazol-5-yl }ethyl)-3-methylpiperazinyl]-1-(2-methylbenzothiazol-5-yloxy)propan-2-ol;
(2S)-1-(2-methylbenzothiazol-5-yloxy)-3-(4-{[3-(4-phenylphenyl)isoxazol-5-yl]methyl}piperazinyl)propan-2-ol;
(2S)-3-(4-{[3-(2-fluorophenyl)isoxazol-5-yl] methyl}piperazinyl)-1-(2-methylbenzothiazol-5-yloxy) propan-2-ol;
(2S)-3-((2S)-4-{[3-(3,4-dichlorophenyl)isoxazol-5-yl]methyl}-2-methylpiperazinyl)-1-(2-methylbenzothiazol-5-yloxy)propan-2-ol;
(2S)-3-(4-{[3-(2,4-dichlorophenyl)isoxazol-5-yl] methyl}piperazinyl)-1-(2-methylbenzothiazol-5-yloxy) propan-2-ol;
(2S)-3-(4-{[3-(3-trifluoromethylphenyl)isoxazol-5-yl] methyl}piperazinyl)-1-(2-methylbenzothiazol-5-yloxy) propan-2-ol;
(2S)-3-(4-{[3-(4-trifluoromethyloxyphenyl)isoxazol-5-yl] methyl}piperazinyl)-1-(2-methylbenzothiazol-5-yloxy) propan-2-ol;
(2S)-3-(4-{[3-(3,4-dichlorophenyl)isoxazol-5-yl] methyl}piperazinyl)-1-(2-methylbenzothiazol-5-yloxy) propan-2-ol;
(2S)-3-(4-{[3-(2-fluorophenyl)isoxazol-5-yl] methyl}piperazinyl)-1-(2-methylbenzothiazol-5-yloxy) propan-2-ol;
(2S)-3-(4-{[3-(4-chlorophenyl)isoxazol-5-yl] methyl}piperazinyl)-1-(2-methylbenzothiazol-5-yloxy) propan-2-ol;
(2S)-3-(4-{[3-(2,3-dichlorophenyl)isoxazol-5-yl] methyl}piperazinyl)-1-(2-methylbenzothiazol-5-yloxy) propan-2-ol;
(2S)-3-(4-{[3-(4-phenylethynylphenyl)isoxazol-5-yl] methyl}piperazinyl)-1-(2-methylbenzothiazol-5-yloxy) propan-2-ol; and
(2S)-3-((2S,5S)-4-{[3-(2,6-dichlorophenyl)isoxazol-5-yl] methyl}-2,5-dimethylpiperazinyl)-1-(2-methylbenzothiazol-5-yloxy)propan-2-ol.

D. Preparation of a Compound of Formula I, varying $R^1$, $R^2$, $R^3$, $R^4$, $R^5$, $R^6$, $R^7$ $R^8$, T, $X^1$, $X^2$, $Z^1$ and $Z^2$ Similarly, following the procedure of Example 11 above, but optionally replacing (2S)-1-(2-methylbenzothiazol-5-yloxy)-3-(4-prop-2-ynylpiperazinyl)propan-2-ol with other compounds of formula (26), and optionally replacing 2,3 dichlorobenzaldehyde oxime with other oximes of formula $X^1$—CH=NOH, other compounds of Formula I are prepared.

EXAMPLE 12

Preparation of a Compound of Formula (30)

Preparation of a Compound of Formula (30) in which $X^1$ is 4-Fluorophenyl

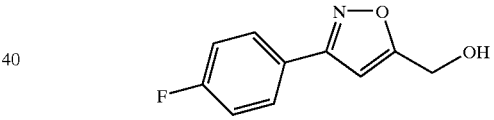

A. Preparation of a Compound of Formula (29) in which $X^1$ is 4-Fluorophenyl

To a stirred solution of N-chlorosuccinimide (0.53 g, 4.00 mmol) in methylene chloride (20 mL) was added syn-4-fluorobenzaldoxime (0.56 g, 4.00 mmol) in one portion. The resulting mixture was stirred at room temperature for 3 hours. Propargyl acetate (0.10 g, 1.00 mmol) was then added in one portion, followed by triethylamine (0.28 mL, 2.00 mmol) in methylene chloride (5 mL) over a period of 20 min. The resulting mixture was stirred at room temperature overnight. The solvent was removed under reduced pressure, and the residue was purified by prep-TLC (ethyl acetate:hexanes=1:4) to give [3-(4-fluorophenyl)isoxazol-5-yl]methyl acetate.

B. Preparation of a Compound of Formula (30) in which $X^1$ is 4-Fluorophenyl

[3-(4-fluorophenyl)isoxazol-5-yl]methyl acetate was stirred in a mixture of aqueous 2N sodium hydroxide (1.60 g, 20 mL $H_2O$) and ethanol (10 mL) at room temperature for 2 hours. The reaction mixture was then neutralized with 2N HCl aqueous solution (20 mL), and extracted with ethyl acetate (2×30 mL). The combined organic layers were dried over sodium sulfate and solvent removed under reduced pressure, to provide [3-(4-fluorophenyl)isoxazol-5-yl]methan-1-ol.

C. Conversion of a Compound of Formula (30) in which $X^1$ is 4-Fluorophenyl to a Mesylate To a stirred solution of [3-(4-fluorophenyl)isoxazol-5-yl]methan-1-ol in tetrahydrofuran (20 mL) in an ice-bath was added triethylamine (0.52 mL, 3.73 mmol) slowly, followed by methanesulfonyl chloride (0.19 mL, 2.49 mmol). The resulting mixture was stirred at 0° C. for 1 hour, then partitioned between ethyl acetate (40 mL) and water (30 mL). The organic layer was further washed with water (3×20 mL), dried over sodium sulfate, and concentrated under reduced pressure.

The following examples illustrate the preparation of representative pharmaceutical formulations containing a compound of Formula I, such as those prepared in accordance with Example 4.

EXAMPLE 13

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 14

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 15

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 16

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 17

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 18

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water.

The sodium benzoate, flavor, and color are diluted with some of the water and added with stirring. Sufficient water is then added to produce the required volume.

EXAMPLE 19

A subcutaneous formulation may be prepared as follows:

| Ingredient | Quantity |
|---|---|
| Active Ingredient | 5.0 mg |
| Corn Oil | 1.0 mL |

EXAMPLE 20

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 21

A topical preparation is prepared having the following composition:

| Ingredients | grams |
|---|---|
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 22

Sustained Release Composition

| Ingredient | Weight Range (%) | Preferred Range (%) | Most Preferred |
|---|---|---|---|
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 10 to 1100 mg of compound free base. Preferably, the tablets will include amounts of compound free base ranging from 10–500 mg, and 20–400 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 23

Mitochondrial Assays

Rat heart mitochondria were isolated by the method of Nedergard and Cannon (Methods in Enzymol. 55, 3, 1979).

Palmitoyl CoA oxidation—The Palmitoyl CoA oxidation was carried out in a total volume of 100 micro liters containing the following agents: 110 mM KCl, 33 mM Tris buffer at pH 8, 2 mM KPi, 2 mM $MgCl_2$, 0.1 mM EDTA, 14.7 microM defatted BSA, 0.5 mM malic acid, 13 mM carnitine, 1 mM ADP, 52 micrograms of mitochondrial protein, and 16 microM 1-C14 palmitoyl CoA (Sp. Activity 60 mCi/mmole; 20 microCi/ml, using 5 microliters per assay). The compounds of this invention were added in a DMSO solution at the following concentrations: 100 micro molar, 30 micro molar, and 3 micro molar. In each assay, a DMSO control was used. After 15 min at 30° C., the enzymatic reaction was centrifuged (20,000 g for 1 min), and 70 microliters of the supernatant was added to an activated reverse phase silicic acid column (approximately 0.5 ml of silicic acid). The column was eluted with 2 ml of water, and 0.5 ml of the eluent was used for scintillation counting to determine the amount of $C^{14}$ trapped as $C^{14}$ bicarbonate ion.

The compounds of the invention showed activity as fatty acid oxidation inhibitors in this assay.

EXAMPLE 24

Perfusate

Langendorff perfusion was conducted using a Krebs-Henseleit solution containing: (mM) NaCl (118.0), KCl (4.7), $KH_2PO_4$ (1.2), $MgSO_4$ (1.2), $CaCl_2$ (2.5), $NaHCO_3$ (25.0) and glucose (5.5 or 11) (Finegan et al. 1996). The working heart perfusate consisted of a Krebs-Henseleit solution with the addition of palmitate (0.4 or 1.2 mM) pre-bound to 3% bovine serum albumin (essentially fatty acid free BSA) and insulin (100 µU/ml). Palmitate was initially dissolved in an ethanol:water mixture (40%:60%) containing 0.5–0.6 g $Na_2CO_3$ per g of palmitate. Following heating to evaporate the ethanol, this mixture was then added to the 3% BSA-Krebs-Henseleit mixture (without glucose) and allowed to dialyze (8000 MW cut-off) overnight in 10 volumes of glucose-free Krebs-Henseleit solution. The next day, glucose was added to the solution and the mixture was filtered through glass microfiber filters (GF/C, Whatman, Maidstone, England) and kept on ice, or refrigerated, prior to use. The perfusate was continuously oxygenated with a 95% $CO_2$, 5% $O_2$ gas mixture while in the perfusion apparatus to main aerobic conditions.

Heart Perfusion Protocols

Rats were anesthetized with pentobarbital (60 mg/kg, intraperitoneally) and hearts were rapidly removed and placed in ice-cold Krebs-Henseleit solution. The hearts were then rapidly cannulated via the aortic stump and Langendorff perfusion at constant pressure (60 mm Hg) was initiated and continued for a 10-min equilibration period. During this equilibration period, the pulmonary artery was cut, and excess fat and lung tissue removed to reveal the pulmonary vein. The left atrium was cannulated and connected to the preload line originating from the oxygenation chamber. After the 10-min equilibration period, hearts were switched to working mode (by clamping off the Langendorff line and opening the preload and afterload lines) and perfused at 37° C. under aerobic conditions at a constant left atrial preload (11.5 mm Hg) and aortic afterload (80 mm Hg). The compliance chamber was filled with air adequate to maintain developed pressure at 50–60 mm Hg. Perfusate was delivered to the oxygenation chamber via a peristaltic pump from the reservoir chamber that collected aortic and coronary flows as well as overflow from the oxygenator.

Typically, hearts were perfused under aerobic conditions for 60 min. Hearts were paced at 300 beats/min throughout each phase of the perfusion protocol (voltage adjusted as necessary) with the exception of the initial 5 min of reperfusion when hearts were allowed to beat spontaneously.

At the end of the perfusion protocol, hearts were rapidly frozen using Wollenberger clamps cooled to the temperature of liquid nitrogen. Frozen tissues were pulverized and the resulting powders stored at −80° C.

Myocardial Mechanical Function

Aortic systolic and diastolic pressures were measured using a Sensonor (Horten Norway) pressure transducer attached to the aortic outflow line and connected to an AD Instruments data acquisition system. Cardiac output, aortic flow and coronary flow (cardiac output minus aortic flow) were measured (ml/min) using in-line ultrasonic flow probes connected to a Transonic T206 ultrasonic flow meter. Left ventricular minute work (LV work), calculated as cardiac output x left ventricular developed pressure (aortic systolic pressure—preload pressure), was used as a continuous index of mechanical function. Hearts were excluded if LV work decreased more than 20% during the 60-min period of aerobic perfusion.

Myocardial Oxygen Consumption and Cardiac Efficiency

Measuring the atrial-venous difference in oxygen content of the perfusate and multiplying by the cardiac output provides an index of oxygen consumption. Atrial oxygen content (mmHg) was measured in perfusate in the preload line or just prior to entering the left atria. Venous oxygen content was measured from perfusate exiting the pulmonary artery and passing through in-line $O_2$ probes and meters Microelectrodes Inc., Bedford, N.H. Cardiac efficiency was calculated as the cardiac work per oxygen consumption.

Measurement of Glucose and Fatty Acid Metabolism

Determining the rate of production of $^3H_2O$ and $^{14}CO_2$ from $[^3H/^{14}C]$glucose in the isolated working rat model allows a direct and continuous measure of the rates of glycolysis and glucose oxidation. Alternatively, the measure of the production of $^3H_2O$ from $[5-^3H]$palmitate provides a direct and continuous measure of the rate of palmitate oxidation. Dual labelled substrates allows for the simultaneous measure of either glycolysis and glucose oxidation or fatty acid oxidation and glucose oxidation. A 3-ml sample of perfusate was taken from the injection port of the recirculating perfusion apparatus at various time-points throughout the protocol for analysis of $^3H_2O$ and $^{14}CO_2$ and immediately placed under mineral oil until assayed for metabolic product accumulation. Perfusate was supplemented with $[^3H/^{14}C]$glucose or $[5-^3H]$palmitate to approximate a specific activity of 20 dpm/mmol. Average rates of glycolysis and glucose oxidation were calculated from linear cumulative time-courses of product accumulation between 15 and 60 min for aerobic perfusion. Rates of glycolysis and glucose oxidation are expressed as mol glucose metabolized/min/g dry wt.

Measurement of Myocardial Glycolysis

Rates of glycolysis were measured directly as previously described (Saddik & Lopaschuk, 1991) from the quantitative determination of $^3H_2O$ liberated from radiolabeled $[5-^3H]$ glucose at the enolase step of glycolysis. Perfusate samples were collected at various time-points throughout the perfusion protocol. $^3H_2O$ was separated from the perfusate by passing perfusate samples through columns containing Dowex 1-X 4 anion exchange resin (200–400 mesh). A 90 g/L Dowex in 0.4 M potassium tetraborate mixture was stirred overnight after which 2 ml of the suspension was loaded into separation columns and washed extensively with $dH_2O$ to remove the tetraborate. The columns were found to exclude 98–99.6% of the total $[^3H]$glucose (Saddik & Lopaschuk, 1996). Perfusate samples (100 µl) were each loaded onto the columns and washed with 1.0 ml $dH_2O$. Effluent was collected in 5 ml of Ecolite Scintillation Fluid (ICN, Radiochemicals, Irvine, Calif.) and counted for 5 min in a Beckman LS 6500 Scintillation Counter with an automatic dual ($^3H/^{14}C$) quench correction program. Average rates of glycolysis for each phase of perfusion are expressed as µmol glucose metabolized/min/g dry wt as described above.

Measurement of Myocardial Glucose Oxidation

Glucose oxidation was also determined directly as previously described (Saddik & Lopaschuk, 1991) by measuring $^{14}CO_2$ from $[^{14}C]$glucose liberated at the level of pyruvate dehydrogenase and in the Krebs cycle. Both $^{14}CO_2$ gas exiting the oxygenation chamber and $[^{14}C]$bicarbonate retained in solution were measured. Perfusate samples were collected at various time-points throughout the perfusion protocol. $^{14}CO_2$ gas was collected by passing the gas exiting the oxygenator through a hyamine hydroxide trap (20–50 ml depending on perfusion duration). Perfusate samples (2×1 ml), which were stored under oil to prevent the escape of gas by equilibration with atmospheric $CO_2$, were injected into 16×150 mm test tubes containing 1 ml of 9 N $H_2SO_4$. This process releases $^{14}CO_2$ from the perfusate present as $H^{14}CO_3^-$. These duplicate tubes were sealed with a rubber stopper attached to a 7-ml scintillation vial containing a 2×5 cm piece of filter paper saturated with 250 µl of hyamine hydroxide. The scintillation vials with filter papers were then removed and Ecolite Scintillation Fluid (7 ml) added. Samples were counted by standard procedures as described above. Average rates of glucose oxidation for each phase of perfusion are expressed as µmol glucose metabolized/min/g dry wt as described above.

Measurement of Myocardial Fatty Acid Oxidation

Rates of palmitate oxidation were measured directly as previously described (Saddik & Lopaschuk, 1991) from the quantitative determination of $^3H_2O$ liberated from radiolabeled [5-$^3H$]palmitate. $^3H_2O$ was separated from [5-$^3H$] palmitate following a chloroform:methanol (1.88 ml of 1:2 v/v) extraction of a 0.5 ml sample of buffer then adding 0.625 ml of chloroform and 0.625 ml of a 2M KCL:HCl solution. The aqueous phase was removed and treated with a mixture of chloroform, methanol and KCl:HCl (1:1:0.9 v/v). Duplicate samples were taken from the aqueous phase for liquid scintillation counting and rates of oxidation were determined taking into account a dilution factor. This results in >99% extraction and separation of $^3H_2O$ from [5-$^3H$] palmitate. Average rates of glucose oxidation for each phase of perfusion are expressed as µmol glucose metabolized/min/g dry wt as described above.

Dry to Wet Ratios

Frozen ventricles were pulverized at the temperature of liquid nitrogen with a mortar and pestle. Dry to wet determinations were made by weighing a small amount of frozen heart tissue and re-weighing that same tissue after 24–48 hr of air drying and taking the ratio of the two weights. From this ratio, total dry tissue could be calculated. This ratio was used to normalize, on a per g dry weight basis, rates of glycolysis, glucose oxidation and glycogen turnover as well as metabolite contents.

The compounds of the invention showed activity as fatty acid oxidation inhibitors in this assay.

References

1. Finegan B A, Gandhi M, Lopaschuk G D, Clanachan A S, 1996. Antecedent ischemia reverses effects of adenosine on glycolysis and mechanical function of working hearts. *American Journal of Physiology* 271: H2116–25.
2. Saddik M, Lopaschuk G D, 1991. Myocardial triglyceride turnover and contribution to energy substrate utilization in isolated working rat hearts. *Journal of Biological Chemistry* 266: 8162–8170.

While the present invention has been described with reference to the specific embodiments thereof, it will be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A compound of the formula:

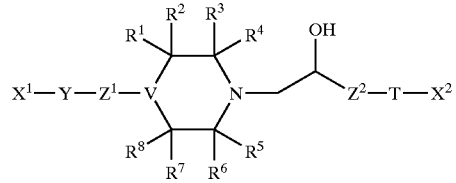

Formula I wherein:
$R^1$, $R^2$, $R^3$, $R^4$, $R^5$, $R^6$, $R^7$, and $R^8$ are hydrogen, lower alkyl, or —C(O)R; in which R is —OR$^9$ or NR$^9R^{10}$, where $R^9$ and $R^{10}$ are hydrogen or lower alkyl; or $R^1$ and $R^2$, $R^3$ and $R^4$, $R^5$ and $R^6$, $R^7$ and $R^8$, when taken together with the carbon to which they are attached, represent carbonyl; or $R^1$ and $R^5$, or $R^1$ and $R^7$, or $R^3$ and $R^5$, or $R^3$ and $R^7$, when taken together form a bridging group —(CR$^{12}R^{13})_n$—, in which n is 1, 2 or 3, and $R^{12}$ and $R^{13}$ are independently hydrogen or lower alkyl;

with the proviso that
(a) the maximum number of carbonyl groups is 2;
(b) the maximum number of —C(O)NR$^9R^{10}$ groups is 1; and
(c) the maximum number of bridging groups is 1;

T is oxygen, or NR$^{11}$, in which $R^{11}$ is hydrogen or lower alkyl;

V is —N<, $X^1$ is optionally substituted cycloalkyl, optionally substituted aryl, or optionally substituted heteroaryl;

$X^2$ is optionally substituted aryl or optionally substituted heteroaryl;

Y is optionally substituted monocyclic heteroarylenyl; and $Z^1$ and $Z^2$ are independently optionally substituted alkylene of 1–4 carbon atoms.

2. The compound of claim 1, wherein T is oxygen.
3. The compound of claim 2, wherein $R^1$, $R^2$, $R^3$, $R^4$, $R^5$, $R^6$, $R^7$ and $R^8$ are independently chosen from hydrogen and methyl.
4. The compound of claim 3, wherein $X^1$ is optionally substituted aryl or optionally substituted heteroaryl.
5. The compound of claim 4, wherein $X^1$ is optionally substituted phenyl, and $X^2$ is optionally substituted phenyl or optionally substituted bicyclic heteroaryl.
6. The compound of claim 5, wherein Y is a diradical derived from pyrazole, 1,2-oxazole, 1,3-oxazole, 1,3-thiazole, 1,2,4-oxadiazole, or 1,3,4-oxadiazole.
7. The compound of claim 6, wherein $X^2$ is 2-methylbenzothiazol-5-yl, 2-cyclohexylbenzothiazol-5-yl, 2-phenylbenzothiazol-5-yl, or 2-phenylbenzoxazol-5-yl.
8. The compound of claim 7, wherein $R^1$, $R^2$, $R^3$, $R^4$, $R^5$, $R^6$, $R^7$ and $R^8$ are all hydrogen.
9. The compound of claim 8, wherein $Z^1$ and $Z^2$ are both methylene.
10. The compound of claim 9, wherein $X^1$ is phenyl optionally substituted by lower alkyl, lower alkoxy, halogen, phenyl, or trifluoromethyl.

11. The compound of claim 10, wherein $X^1$—Y— is 3-(4-t-butylphenyl)-1,2,4-oxadiazol-5-yl and $X^2$ is 2-methylbenzothiazol-5-yl, namely 3-{4-[3-(4-t-butylphenyl)-[1,2,4]oxadiazol-5-ylmethyl]-piperazin-1-yl}-1-(2-methylbenzothiazol-5-yloxy)-propan-2-ol.

12. The compound of claim 10, wherein $X^1$—Y— is 5-(4-trifluoromethylphenyl)-1,2,4-oxadiazol-3-yl and $X^2$ is 2-methylbenzothiazol-5-yl, namely 3-{4-[5-(4-(trifluoromethyl)phenyl)-[1,2,4]oxadiazol-3-ylmethyl]-piperazin-1-yl}-1-(2-methyl-benzothiazol-5-yloxy)-propan-2-ol.

13. The compound of claim 7, wherein one of $R^1$, $R^2$, $R^3$, $R^4$, $R^5$, $R^6$, $R^7$ and $R^8$ is methyl and the remainder are hydrogen.

14. The compound of claim 13, wherein $Z^1$ and $Z^2$ are both methylene.

15. The compound of claim 14, wherein $X^1$ is phenyl optionally substituted by lower alkyl, lower alkoxy, halogen, or trifluoromethyl.

16. The compound of claim 15, wherein $R^4$ is methyl and $R^1$, $R^2$, $R^3$, $R^5$, $R^6$, $R^7$ and $R^8$ are hydrogen.

17. The compound of claim 16, wherein $X^1$—Y— is 5-(4-(trifluoromethyl)phenyl)-1,2,4-oxadiazol-3-yl and $X^2$ is 2-methylbenzothiazol-5-yl, namely (2S)-3-[(2S)-2-methyl-4-({5-[4-(trifluoromethyl)phenyl](1,2,4-oxadiazol-3-yl)}methyl)piperazinyl]-1-(2-methylbenzothiazol-5-yloxy)propan-2-ol.

18. The compound of claim 16, wherein $X^1$—Y— is 5-[4-chlorophenyl]isoxazol-3-yl and $X^2$ is 2-methylbenzothiazol-5-yl, namely (2S)-3-[(2S)-2-methyl-4-({5-[4-chlorophenyl]isoxazol-3-yl}methyl)piperazinyl]-1-(2-methylbenzothiazol-5-yloxy)propan-2-ol.

19. The compound of claim 16, wherein $X^1$—Y— is 5-[2-chlorophenyl]isoxazol-3-yl and $X^2$ is 2-methylbenzothiazol-5-yl, namely (2S)-3-[(2S)-2-methyl-4-({5-[2-chlorophenyl]isoxazol-3-yl}methyl)piperazinyl]-1-(2-methylbenzothiazol-5-yloxy)propan-2-ol.

20. The compound of claim 16, wherein $X^1$—Y— is 5-[4-(trifluoromethyl)phenyl](1,2,4-oxadiazol-3-yl) and $X^2$ is 2-methylbenzothiazol-5-yl, namely (2S)-3-[(2S)-2-methyl-4-({5-[4-(trifluoromethyl)phenyl](1,2,4-oxadiazol-3-yl)}methyl)piperazinyl]-1-(2-methylbenzothiazol-5-yloxy)propan-2-ol.

21. The compound of claim 16, wherein $X^1$—Y— is 5-(3,4-dichlorophenyl)isoxazol-3-yl and $X^2$ is 2-methylbenzothiazol-5-yl, namely (2S)-3-((2S)-4-{[5-(3,4-dichlorophenyl)isoxazol-3-yl]methyl}-2-methylpiperazinyl)-1-(2-methylbenzothiazol-5-yloxy)propan-2-ol.

22. The compound of claim 16, wherein $X^1$—Y— is 3-phenylisoxazol-5-yl and $X^2$ is 2-methylbenzothiazol-5-yl, namely (2S)-3-{(2S)-2-methyl-4-[(3-phenylisoxazol-5-yl)methyl]piperazinyl}-1-(2-methylbenzothiazol-5-yloxy)propan-2-ol.

23. The compound of claim 16, wherein $X^1$—Y— is 3-(4-methoxyphenyl)isoxazol-5-yl and $X^2$ is 2-methylbenzothiazol-5-yl, namely (2S)-3-{(2S)-2-methyl-4-[(3-(4-methoxyphenyl)isoxazol-5-yl)methyl]piperazinyl}-1-(2-methylbenzothiazol-5-yloxy)propan-2-ol.

24. The compound of claim 16, wherein $X^1$—Y— is 5-phenylisoxazol-3-yl) and $X^2$ is 2-methylbenzothiazol-5-yl, namely 3-{(2S)-2-methyl-4-[(5-phenylisoxazol-3-yl)methyl]piperazinyl}(2S)-1-(2-methylbenzothiazol-5-yloxy)propan-2-ol.

25. The compound of claim 16, wherein $X^1$—Y— is 3-(2-thienyl)(1,2,4-oxadiazol-5-yl and $X^2$ is 2-methylbenzothiazol-5-yl, namely (2S)-3-{(2S)-2-methyl-4-[(3-(2-thienyl)(1,2,4-oxadiazol-5-yl)methyl]piperazinyl}-1-(2-methylbenzothiazol-5-yloxy)propan-2-ol.

26. The compound of claim 16, wherein $X^1$—Y— is 2-[4-(trifluoromethyl)phenyl](1,3-oxazol-5-yl) and $X^2$ is 2-methylbenzothiazol-5-yl, namely (2S)-3-[(2S)-2-methyl-4-({2-[4-(trifluoromethyl)phenyl](1,3-oxazol-5-yl)}methyl)piperazinyl]-1-(2-methylbenzothiazol-5-yloxy)propan-2-ol.

27. The compound of claim 15, wherein $R^8$ is methyl and $R^1$, $R^2$, $R^3$, $R^4$, $R^5$, $R^6$, and $R^7$ are hydrogen.

28. The compound of claim 27, wherein $X^1$—Y— is 3-(4-methoxyphenyl)isoxazol-5-yl and $X^2$ is 2-methylbenzothiazol-5-yl, namely (2S)-3-{(3S)-3-methyl-4-[(3-(4-methoxyphenyl)isoxazol-5-yl)methyl]piperazinyl}-1-(2-methylbenzothiazol-5-yloxy)propan-2-ol.

29. The compound of claim 27, wherein $X^1$—Y— is 5-(3,4-dichlorophenyl)isoxazol-3-yl and $X^2$ is 2-methylbenzothiazol-5-yl, namely (2S)-3-{(3S)-3-methyl-4-[(5-(3,4-dichlorophenyl)isoxazol-3-yl)methyl]piperazinyl}-1-(2-methylbenzothiazol-5-yloxy)propan-2-ol.

30. The compound of claim 27, wherein $X^1$—Y— is 5-(2-chlorophenyl)isoxazol-3-yl and $X^2$ is 2-methylbenzothiazol-5-yl, namely (2S)-3-{(3S)-3-methyl-4-[(5-(2-chlorophenyl)isoxazol-3-yl)methyl]piperazinyl}-1-(2-methylbenzothiazol-5-yloxy)propan-2-ol.

31. The compound of claim 27, wherein $X^1$—Y— is 5-(4-chlorophenyl)isoxazol-3-yl and $X^2$ is 2-methylbenzothiazol-5-yl, namely (2S)-3-{(3S)-3-methyl-4-[(5-(4-chlorophenyl)isoxazol-3-yl)methyl]piperazinyl}-1-(2-methylbenzothiazol-5-yloxy)propan-2-ol.

32. The compound of claim 27, wherein $X^1$—Y— is 5-(4-trifluoromethylphenyl)-isoxazol-3-yl and $X^2$ is 2-methylbenzothiazol-5-yl, namely (2S)-3-((3S)-3-methyl-4-{[5-(4-trifluoromethylphenyl)isoxazol-3-yl]methyl}-piperazinyl)-1-(2-methylbenzothiazol-5-yloxy)propan-2-ol.

33. The compound of claim 27, wherein $X^1$—Y— is 5-(4-phenylphenyl)isoxazol-3-yl and $X^2$ is 2-methylbenzothiazol-5-yl, namely (2S)-3-((3S)-3-methyl-4-{[5-(4-phenylphenyl)isoxazol-3-yl]methyl}piperazinyl)-1-(2-methylbenzothiazol-5-yloxy)propan-2-ol.

34. The compound of claim 27, wherein $X^1$—Y— is 5-(3,4-dichlorophenyl)isoxazol-3-yl and $X^2$ is 2-methylbenzothiazol-5-yl, namely (2S)-3-{(3S)-3-methyl-4-[(5-(3,4-dichlorophenyl)isoxazol-3-yl)methyl]piperazinyl}-1-(2-methylbenzothiazol-5-yloxy)propan-2-ol.

35. A pharmaceutical composition comprising at least one pharmaceutically acceptable excipient and a therapeutically effective amount of a compound of claim 1.

* * * * *